United States Patent
Ciupik

(10) Patent No.: US 9,198,771 B2
(45) Date of Patent: Dec. 1, 2015

(54) INTERVERTEBRAL IMPLANT FOR MUTUAL SITUATING OF ADJACENT VERTEBRAE

(75) Inventor: Lechoslaw Franciszek Ciupik, Zielona Gora (PL)

(73) Assignee: LFC SPOLKA Z O.O., Zielona Gora (PL)

( * ) Notice: Subject to any disclaimer, the term of this patent is extended or adjusted under 35 U.S.C. 154(b) by 0 days.

(21) Appl. No.: 14/117,351

(22) PCT Filed: May 11, 2012

(86) PCT No.: PCT/PL2012/000031
§ 371 (c)(1),
(2), (4) Date: Nov. 12, 2013

(87) PCT Pub. No.: WO2012/154068
PCT Pub. Date: Nov. 15, 2012

(65) Prior Publication Data
US 2014/0088715 A1    Mar. 27, 2014

(30) Foreign Application Priority Data

May 12, 2011   (PL) .......................................... 394841

(51) Int. Cl.
*A61F 2/44*     (2006.01)
*A61F 2/30*     (2006.01)
*A61F 2/46*     (2006.01)

(52) U.S. Cl.
CPC ................. *A61F 2/442* (2013.01); *A61F 2/447* (2013.01); *A61F 2/4455* (2013.01); *A61F 2/4611* (2013.01); *A61F 2002/3052* (2013.01); *A61F 2002/30143* (2013.01); *A61F 2002/30171* (2013.01); *A61F 2002/30266* (2013.01); *A61F 2002/30281* (2013.01); *A61F 2002/30364* (2013.01); *A61F 2002/30365* (2013.01);

(Continued)

(58) Field of Classification Search
CPC ............................... A61F 2/442; A61F 2/4611
USPC ........................................... 623/17.11, 17.16
See application file for complete search history.

(56) References Cited

U.S. PATENT DOCUMENTS 5,697,977 A    12/1997  Pisharodi
5,888,228 A *  3/1999   Knothe et al. ............. 623/17.16

(Continued)

FOREIGN PATENT DOCUMENTS

| | | |
|---|---|---|
| EP | 1210920 A1 | 6/2002 |
| EP | 2181674 A1 | 5/2010 |
| WO | 9848738 A1 | 11/1998 |
| WO | 0016711 A2 | 3/2000 |
| WO | 0166048 A1 | 9/2001 |
| WO | 2010028056 A1 | 3/2010 |
| WO | 2011037484 A1 | 3/2011 |

OTHER PUBLICATIONS

International Search Report and Written Opinion of the International Searching Authority re PCT/PL2012/000031; dated Oct. 5, 2012.

*Primary Examiner* — Jerry Cumberledge
*Assistant Examiner* — Tessa Matthews
(74) *Attorney, Agent, or Firm* — Hovey Williams LLP

(57) ABSTRACT

An intervertebral implant for mutual situating of adjacent vertebrae includes a cover and a driving mechanism mounted in the cover. The cover presents a manipulative hole and a seat. The driving mechanism is located in the seat and includes a rotational element with anchoring to engage a vertebra. The implant includes a connecting element located within the diameter of the manipulative hole and operable to be engaged by a driving tool.

28 Claims, 32 Drawing Sheets

(52) U.S. Cl.
CPC ............... *A61F 2002/30367* (2013.01); *A61F 2002/30492* (2013.01); *A61F 2002/30494* (2013.01); *A61F 2002/30522* (2013.01); *A61F 2002/30523* (2013.01); *A61F 2002/30525* (2013.01); *A61F 2002/30527* (2013.01); *A61F 2002/30553* (2013.01); *A61F 2002/30818* (2013.01); *A61F 2002/30836* (2013.01); *A61F 2002/30841* (2013.01); *A61F 2002/30843* (2013.01); *A61F 2002/30845* (2013.01); *A61F 2002/30846* (2013.01); *A61F 2002/30848* (2013.01); *A61F 2002/30904* (2013.01); *A61F 2002/4475* (2013.01)

(56) References Cited

U.S. PATENT DOCUMENTS

| | | | |
|---|---|---|---|
| 6,210,442 | B1 | 4/2001 | Wing et al. |
| 6,491,695 | B1 | 12/2002 | Roggenbuck |
| 2002/0161445 | A1* | 10/2002 | Crozet ............ 623/17.11 |
| 2004/0073214 | A1 | 4/2004 | Mehdizadeh |
| 2008/0319481 | A1 | 12/2008 | Moore |
| 2009/0099601 | A1* | 4/2009 | Aferzon et al. ......... 606/246 |
| 2011/0015747 | A1* | 1/2011 | McManus et al. ....... 623/17.16 |
| 2011/0035007 | A1* | 2/2011 | Patel et al. ............. 623/17.11 |

* cited by examiner

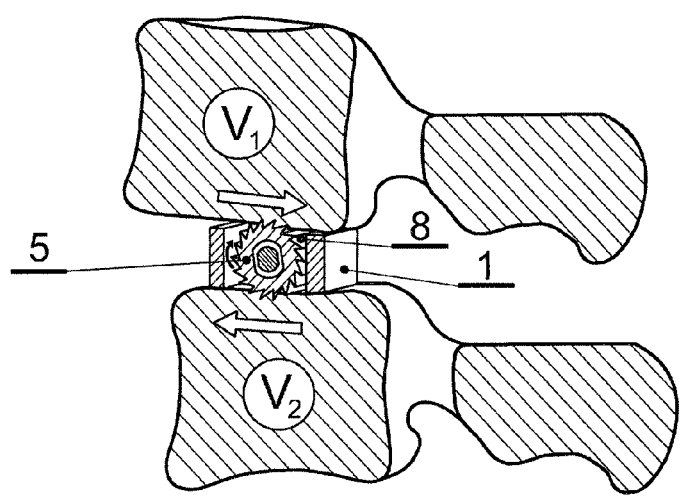
Fig. 26
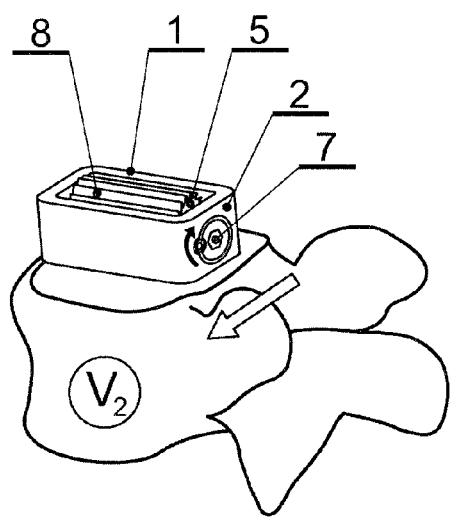 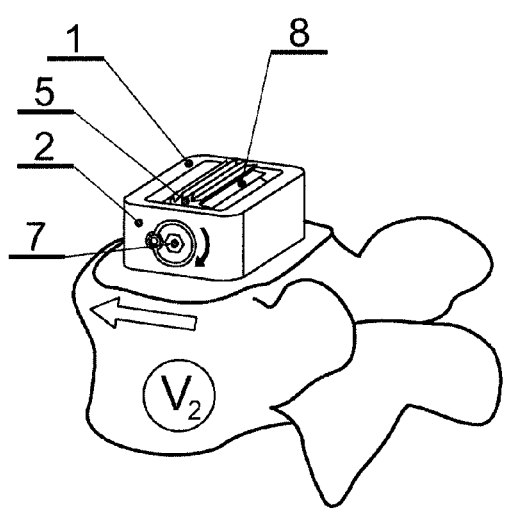
Fig. 27  Fig. 28

INTERVERTEBRAL IMPLANT FOR MUTUAL SITUATING OF ADJACENT VERTEBRAE

CROSS-REFERENCE TO RELATED APPLICATIONS

This is a National Phase Application pursuant to 37 C.F.R. §371 of International Application No. PCT/PL2012/000031, filed May 11, 2012, claiming priority from Polish Application No. P-394841, filed May 12, 2011, each of which is incorporated in its entirety by reference herein.

BACKGROUND

1. Field

The invention relates to an intervertebral implant for mutual situating of adjacent vertebrae, enabling their displacement in sagittal and coronal plane, which can be applicable in the treatment of dysfunctions in all spinal segments, especially in the treatment of spondylolisthesis.

2. Discussion of the Prior Art

From the U.S. Pat. No. 5,888,228 an intervertebral implant is known, which is situated in the intervertebral body space and is designed for achieving the bone fusion, especially in the lumbar spinal segment. The implant is made in a form of a frame-type cage, opened on its top and base faces, it has got lateral surfaces, front wall and rear wall; there is a rotating element mounted in the cage. The outer surface of the rotating element is provided with a helical structure and protrudes beyond top and base face of the cage. The front wall and the rotating element have got an aperture for introduction of the drive tool, with which the rotating element fixed in the cage is rotated. The rotating element can be cylindrical or conical and can have holes. The offered solution acts as an interbody implant, and the rotating element located in the cage serves to introduce/screw the implant into the interbody space. This solution, however, doesn't give any opportunities to displace adjacent vertebrae relative to each other in the coronal or sagittal plane. From the patent application WO 2010/028056 an intervertebral implant is known for insertion into an intervertebral space between two adjacent vertebrae. The implant includes an intervertebral spacer and a spiral anchor coupling to the intervertebral spacer and two adjacent vertebral bodies. The spiral anchor is configured to partially embed within a portion of the vertebral body. The spiral anchor used in the implant fulfils the function of fixing of the implant to vertebrae. Presented solution is a usual intervertebral body cage, which keeps a distance between vertebrae after performed deposition of the intervertebral disc and allows for bone fusion.

From the patent application WO 01/66048 a two-part intervertebral implant is known, which is used for restoration of a spacing between adjacent vertebrae. The implant includes a spacer ring connected with a vertebra and a bore for introducing a locking element, which cooperates with a centre of the spacer's ring. The locking element has got a diameter or a height greater than the thickness of the spacer's ring and serves to lock the implant between two vertebrae. In one embodiment the spacer's ring can be C-shaped. In an alternative embodiment the spacer's ring can have a form of an intact ring having a side bore for receipt of the locking element.

The implant constitutes an intervertebral spacer with locking using the special element. The disadvantage of this solution is a lack of a possibility of displacement of vertebrae according each other by the implant.

From the patent application WO 00/16711 an interbody implant is known, for enhancing fusion of adjacent vertebrae. The implant comprises a form of rectangular cage member with an open construction, having a plurality of ribs for connection with plateaus of adjacent vertebral bodies. Ribs prevent the lateral shifting of the implant. The implant is held against the anterior/posterior motion by a locking screw, which engages the cage and adjacent bone tissue. The cage is adapted to be packed with a bone graft in order to improve bone fusion.

This solution is used to accelerate the bone fusion or to improve the possibility of arising of bone fusion and its aim is maintenance of the height of the intervertebral space, which was surgically restored. The disadvantage of this solution is lack of a possibility of mutual adjustment of vertebrae by the implant. A threaded element in a form of a screw is intended to blocking the implant in the intervertebral space, preventing displacement of the implant forward and backwards.

From the U.S. Pat. No. 6,210,442 is known implant for fusion of vertebral bodies, situated in the space between two adjacent vertebral bodies. The implant has got a supporting body, which opposite surfaces are situated between opposite vertebral bodies to achieve optimal fixation of the supporting body in the intervertebral space. The supporting body has got at least one location channel, which extends between supporting surfaces and is open on its top and bottom side. Into the location channel, there is introduced with rotational movement the fixing element provided with an external projection. The fixing element projects out of the open location channel. This solution is intended for fusing of vertebrae, serving simultaneously a function of an intervertebral spacer. Its construction doesn't allow for vertebral movement against each other.

From the patent application WO 9848738 is known implant for bone surgery comprising situated in the intervertebral space hollowed body with a pair of lateral walls enclosing and defining the intervertebral space and anchoring-reinforcement member, having on its outer surface anchoring projections with a diameter greater than body's overall height. The anchoring-reinforcement member is introduced into the inner space of the body with rotational movement. This solution ensures maintenance of the surgically restored intervertebral body space, serving as a distance-keeping element. It doesn't give, however, the possibility of displacement of vertebrae against each other.

From the patent application EP 1210920 is known a device for spinal fixation comprising main body, two-side pieces and fastening device for their symmetrical fastening with two sides of the main body. Two-side pieces are smaller in thickness than the main body. This solution allows for maintenance of restored during the surgery height of the intervertebral space and fixation leading to a bone fusion.

From the patent application US 2004/073214 is known an apparatus and a method for correction the spondylolisthesis. In this solution are used: a distractor of a discal space and separate correcting instrument for shifting the displaced vertebra into the proper position in a relation to the adjacent vertebra. The separate correcting instrument and the distractor of the discal space are used to perform initial stages of the correction, such as distraction of the discal space and incision of threads connecting with the stabilizing implant, and also for a correction of spondylolisthesis and maintenance of the correction before stabilization. This solution requires placement of an additional implant in the interbody space after the correction. The main disadvantage of this solution is the possibility of losing reposition during the act of changing of correction instrument for a stabilizing implant and increased number of tools required for performance both reposition and stabilization with the implant.

Presented above solutions mainly serve as distance-keeping elements, maintaining surgically restored height of the intervertebral space. The aim of rotational elements in a form of screws or anchors is to block implants between two vertebrae in their proper position, because their construction allows for dention into vertebral bodies. The majority of mentioned solutions don't assure, however, the possibility of displacement according to each other of adjacent vertebrae in a coronal or sagittal plane, especially in a treatment of spondylolisthesis. In turn in the solution US 2004/073214, which allows for mutual displacement of vertebrae, there is a possibility of losing of gained reposition and necessity of using additional implant to stabilize the correction.

SUMMARY

The following summary is provided to indicate the nature of the subject matter disclosed herein. While certain aspects of the present invention are described below, the summary is not intended to limit the scope of the present invention.

The aim of the invention is to assure the displacement of adjacent vertebrae in a relation to each other in a coronal or sagittal plane for more efficient treatment of spinal dysfunctions, especially spondylolisthesis, resolving the problem of maintenance of position of displaced vertebrae in a relation to each other and restriction to the minimum of number of tools or elements used in the treatment of these dysfunctions.

The above mentioned aim is achieved by an intervertebral implant according to claim 1. The depending claims describe further developments of the invention.

An inventive intervertebral implant for mutual situating of adjacent vertebrae contains a driving mechanism fixed in a cover which cover is provided with a cover wall and at least one manipulative hole in the cover wall, where
  the cover is further provided with at least one open seat,
  the driving mechanism comprises at least one rotational element with an axis which rotational element is located in the seat and rotatable about the axis;
  the rotational element is equipped with anchoring latches or groups of anchoring latches projecting over the height of the cover wall where the anchoring latches or the groups of anchoring latches extend parallel to the axis of the rotational element,
  the rotational element cooperates with at least one connecting element situated within the diameter of the a manipulative hole of the cover wall; and
  the implant is provided with at least one blockade for blocking the rotation of the driving mechanism.

In a first implementation of the inventive intervertebral implant the cover may be equipped with at least one anchoring projection projecting over the cover wall in a direction opposite to the direction in which the anchoring latches or groups of anchoring latches of the rotatable element project over the cover wall. In a second implementation of the inventive intervertebral implant the anchoring latches or groups of anchoring latches of the rotational element project over the cover wall in two directions opposite to each other.

The above mentioned aim has been gained using implant for mutual situating of adjacent vertebrae having a driving mechanism fixed in a cover provided with at least one manipulative hole. According to the invention, the cover of the implant is equipped with at least one open seat, and the driving mechanism composes located in the seat and anchoring in one of displaced vertebrae at least one rotational element with an axis mounted for an axial movement in lateral walls of the cover perpendicularly to the direction of displacement of vertebrae in a relation to each other, cooperating with at least one connecting element situated within the diameter of a selected manipulative hole of the cover. The manipulative hole is circular (round) or shaped. The rotational element is equipped with anchoring latches projecting over the height of cover's walls from the side contacting with one of displaced vertebra, fixed in this vertebra during the installation of the implant. The implant is equipped with at least one blockade of rotation of the driving element.

Favorably rotational elements are separated from each other. Rotational elements can be separated by the separating wall or by the fragment of the cover.

Rotational elements of the driving mechanism have equal or various dimensions, anchoring latches situated on the rotational element or on rotational elements have equal or various dimensions, and also equal or various shapes.

In an embodiment of the invention the rotational element is made of seated on a common axis separate parts situated in corresponding to them sections of the seat, separated by at least one separating wall. Separate parts of the rotational element have equal or various dimensions. Anchoring latches situated on a separate part or separate parts of the rotational element have equal or various dimensions, and also equal or various shapes.

In various embodiments of the invention, anchoring latches have a form of spikes, teeth or paddles.

The rotational element is equipped with circular or shaped hole, through which passes the axis of the rotational element. The axis of the rotational element has got a circular or shaped cross section. The axis of the rotational element constitutes its inseparable part or it is fixed separately in the rotational element, when it's cross section is shaped. When the axis has got a shaped cross section, preferably the greatest dimension A of the cross section of the axis is bigger than the transverse dimension B of the hole of the rotational element. Made in this way gap between the axis and the rotational element enables an additional movement up-down and forward-backwards of the rotational element in relation with the axis, allowing for adjustment of the rotational element to the shape of the intervertebral space.

For better cooperation of the rotational element with the connecting element and with separate driving tool, at least one end of the axis of at least one rotational element has got a form of a shaped element, favorably with a hexagon cross section.

In an embodiment of the invention on at least one end of the axis of at least one rotational element a gear is seated.

The connecting element is situated within the diameter of the manipulative hole of the cover and cooperates with a separate driving instrument.

Preferably the connecting element composes at least one end of the axis of at least one rotational element.

In an embodiment of the invention the connecting element has got a form of a gear cooperating with the gear seated on a selected end of the axis of at least one rotational element.

The connecting element can be equipped with a pin or a shaped recess.

There are also possible embodiments of performing connecting element, where it composes the end of the axis with a gear and pin or a shaped and of the axis.

The anchoring projection has got preferably a form of a spike, tooth, or a paddle. Anchoring projections can have various dimensions or shapes.

The blockade of rotation of the driving mechanism has got a form of a pin situated within the diameter of the manipulative hole of the cover and cooperating with the recess in the axis of the rotational element.

In one embodiment the blockade of the rotation of the driving mechanism has got a form of at least one latch fixed to the cover and cooperating with at least one rotational element.

In different embodiments the blockade of the rotation of the driving mechanism has got a form of paddles or teeth situated on the lateral surface of the rotational element cooperating with at least one latch fixed to the cover. The blockade of the rotation of the driving mechanism alternatively has got a form of holes made on the lateral surface of the rotational element cooperating with at least one latch fixed to the cover.

In this embodiment one vertebra is displaced by rotation of the rotational element, which is anchored in this vertebra with anchoring latches. The movement of the displaced vertebra runs in relation to the second vertebra and the cover, which is maintained in the immobile position as a result of anchoring of the anchoring projections in the second vertebra.

The implant according to the invention is characterized by a simple and compact construction, enabling ease of performing the correction, to restore a normal alignment of vertebrae, in the coronal or sagittal plane using the rotational element composing a part of a driving mechanism, with a small strength. The implant enables performance of the correction simultaneously in two planes: sagittally-horizontal or coronally-horizontal, or also in three planes, depending on setting of the implant in the intervertebral space and the surgical approach. The implant can be used in a treatment from posterior, anterior, lateral or mixed approach.

In a process of the correction the rotational element is displaced against the cover and situated to the position assuring maintenance of the contact with opposite surfaces of the endplate. The construction and various embodiments of the rotational element allow for adjustment of the implant to the shape of the intervertebral space. The shape of the rotational element and its location on the axis increase the chance to anchor of anchoring latches of the rotational element in the vertebral bone and situating of the implant in a proper place and in a proper position. Anchoring latches with the blockade of the rotation allow for a control of the blockade of the implant in a proper position achieved after performed correction.

The construction of the connecting element enables connection and cooperation of the implant with a separate surgical tool, and thereby allows for efficient performance of a process of displacement of two adjacent vertebrae in a relation to each other. The cooperation of the driving tool with the axis of the rotational element using the connecting element allows for controlling and quick performance of the correction process.

The cover of the implant composes a bearing element and it supports on the strongest, the most strength elements of bones, and this secures the implant against subsidence and penetration into the vertebral bone. Moreover, the cover corrects the biomechanical balance, fulfills the function of alignment and acts like a driving element.

The implant fulfills biomechanical demands of the stabilization, enables possibility of a surgical installation from various surgical approach and—especially thanks to various shapes of the cover—it adjusts to anatomic shape of the intervertebral space, which assures efficiency of treatment of patients in every age. Moreover, the solution according to the invention assures restoration of proper anatomical proportions and biomechanical balance.

Described in the state of the art inconveniences concerning the lack of possibility of displacement of vertebrae according to each other end necessity of use of greater number of tools or elements used in the treatment of spinal dysfunctions, especially spondylolisthesis, it removes also the intervertebral implant for mutual situating of adjacent vertebrae containing the driving element fixed in the cover provided with at least one manipulative hole. According to the invention, the cover of the implant is equipped with at least one open seat, and the driving mechanism constitutes situated in the seat and anchoring in both displaced vertebrae at least one rotational element with an axis mounted for axial movement in lateral walls of the cover in perpendicular direction to the direction of displacement of vertebrae in a relation to each other, cooperating with at least one connecting element situated within the diameter of selected manipulative hole of the cover. The manipulative hole is circular or shaped. The rotational element is provided with anchoring latches projecting over the height of lateral cover's walls and serving for anchoring of the rotational element in both displaced vertebrae during the process of installation of the implant. The implant is provided with at least one blockade of the rotation of the driving mechanism.

Preferably rotational elements are separated from each other. Rotational elements can be separated by a separating wall or a fragment of a cover.

Rotational elements of the driving mechanism have equal or various dimensions, anchoring latches situated on the rotational element or on rotational elements have equal or various dimensions, and also equal or various shapes.

In an embodiment of the invention the rotational element is made on seated on a common axis separate parts located in corresponding to them, separated by at least one separating wall, sections of the seat. Separate parts of the rotational element have equal or various dimensions. Anchoring latches situated on a separate part of separate parts of the rotational element have equal or various dimensions, and also equal or various shapes.

In various embodiments of the invention anchoring latches have got a form of spikes, teeth or paddles.

The rotational element is equipped with a circular or shaped hole, through which passes the axis of the rotational element. The axis of the rotational element has got a circular or shaped cross-section. The axis of the rotational element constitutes its inseparable part or it is fixed separately in the rotational element, when its cross section is shaped. When the axis composes a shaped element, preferably the greatest dimension A of the cross-section of the axis is greater than the transverse dimension B of the hole of the rotational element. Created in this way recess between the axis and the rotational element enables additional upside-down movement and forward-backwards of the rotational element according to the axis, allowing for adjustment of the rotational element to the shape of the intervertebral body space.

For a better cooperation of the rotational element with the connecting element and a separate driving tool, at least one end on the axis of at least one rotational element has got a form of a shaped element, preferably with a hexagonal cross section.

In an embodiment of the invention on at least one end of the axis of at least one rotational element at least one gear is seated.

The connecting element is situated within the diameter of the manipulative hole of the cover and cooperates with a separate driving tool.

Preferably, the connecting element composes at least one end of the axis of at least one rotational element.

In an embodiment of the invention the connecting element has got a form of a gear cooperating with the gear seated on the selected end of the axis of at least one rotational element.

The connecting element can be equipped with a plug or a shaped recess.

There are possible embodiments of realization of the connecting element, where it composes the end of the axis with a gear and a plug or a shaped end of the axis.

The blockade of the rotation of the driving mechanism has got a form of a pin situated within the diameter of the manipulative hole of the cover and cooperating with a recess in the axis of the rotational element.

In an embodiment the blockade of the rotation of the driving mechanism has got a form of paddles or teeth situated on the lateral surface of the rotational element cooperating with at least one latch fixed to the cover.

The blockade of the rotation of the driving mechanism alternatively has got a form of holes made on the lateral surface of the rotational element cooperating with at least one latch fixed to the cover.

In this solution both vertebrae are displaced according to each other, in an opposite direction, by the rotation of anchored in them rotational element with anchoring latches. Movement of vertebrae takes place also in a relation to the cover. The cover of the implant is not connected to any of displaced vertebrae.

Implant according to the invention is characterized with a simple and compact construction, assuring facility of performance of the correction in order to restore normal adjustment of vertebrae, in coronal or sagittal plane using the rotational element composing a part of the driving mechanism, with the use of a minor force. Implant enables performance of a correction simultaneously in two planes: sagittaly-horizontal or coronary-horizontal, or in three planes, depending on setting of the implant in the intervertebral space and surgical approach. Implant can be used in the treatment from posterior, anterior, lateral and mixed approach. In the process of the correction the rotational element is displaced in a relation to the cover and situated to the position assuring maintenance of the contact with opposite surfaces of the endplate. The construction and various embodiments of the rotational element allow for adjustment of the implant to the shape of the intervertebral space. The shape of the rotational element and its situating on the axis further increases the chance for anchoring of the anchoring latches of the rotational element in the vertebral bone and situating of the implant in a proper place and a proper position. Anchoring latches with the blockade of the rotation allow for a control of blocking of the implant in a proper position acquired after performed correction.

The construction of the connecting element enables connection and cooperation of the implant with a separate surgical driving tool, and thereby allows for efficient performance of a process of displacement of two adjacent vertebrae in the relation to each other. The cooperation of the driving tool with the axis of the rotational element using the connecting element allows for a control and quick realization of the correction process.

The cover of the implant composes a bearing element and it supports on the strongest, the most strength elements of bones, which secures the implant against subsidence and penetration into the vertebral bone. Moreover, the cover corrects the biomechanical balance and fulfills the function of an aligning element. The implant fulfills biomechanical demands of the stabilization, enables possibility of the surgical installation at various surgical approaches and—especially by various shapes of the cover—it adjusts to the anatomic shape of the intervertebral space, which assures efficiency of treatment of patients in every age. Moreover, the solution according to the invention assures restoration of proper anatomical proportions and biomechanical balance.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Solutions according to the invention are presented in examples, which do not restrict its range, in accompanying figures, wherein.

Figure 10:
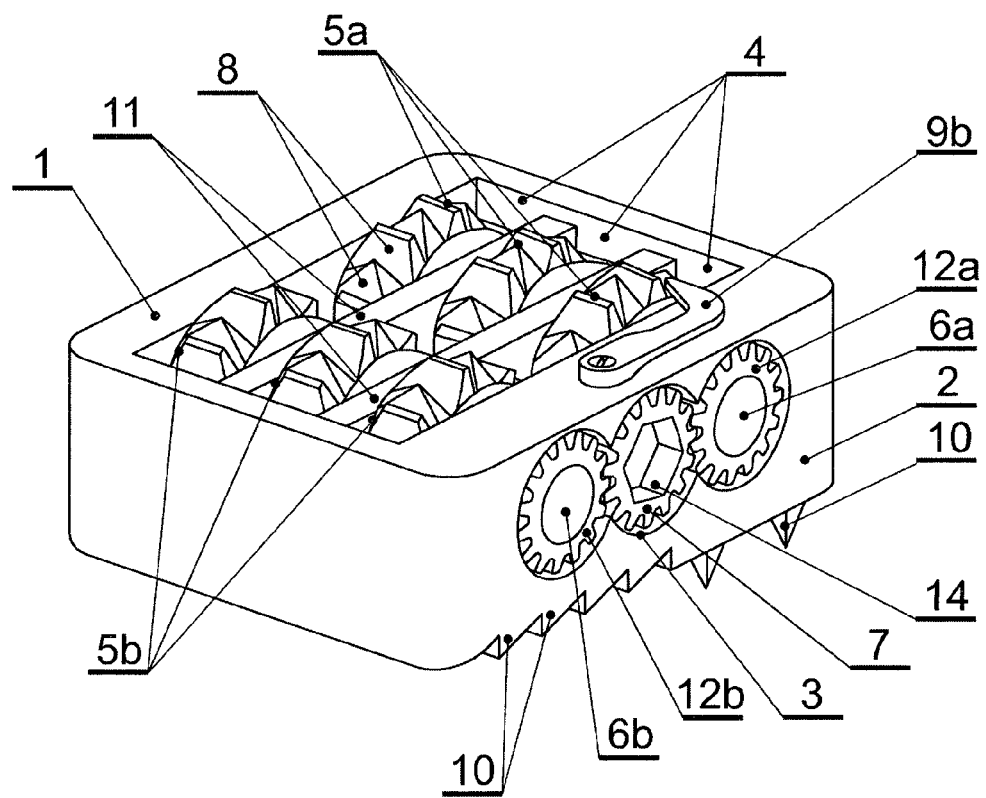
Figure 11:
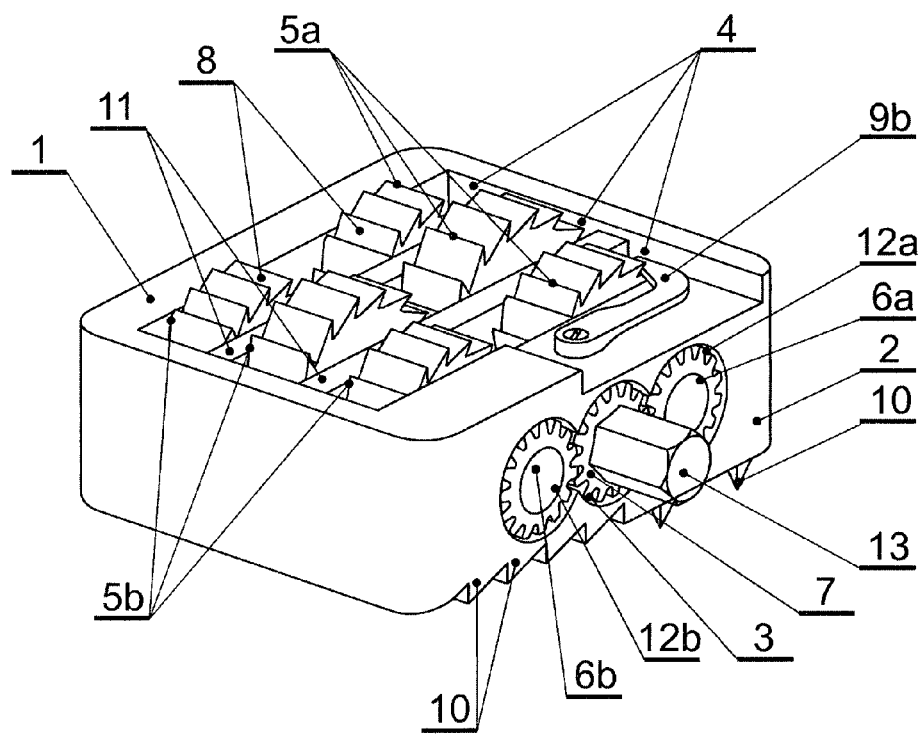
Figure 12:
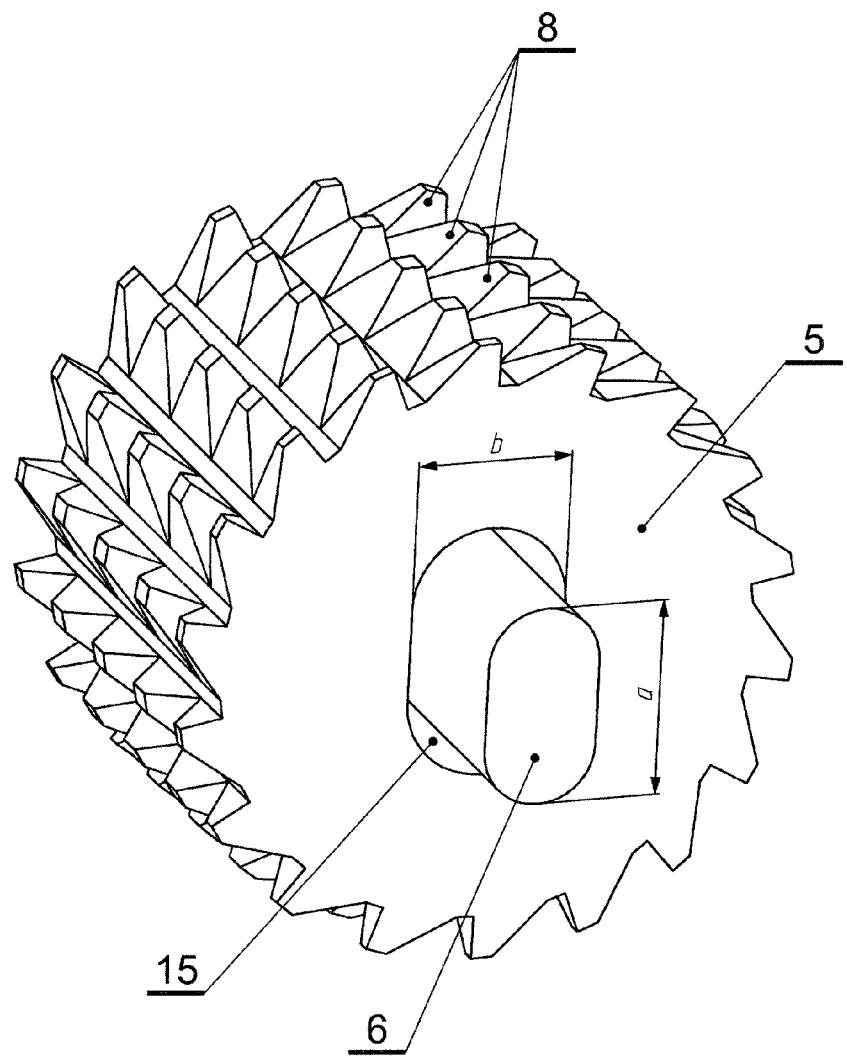
Figure 13:
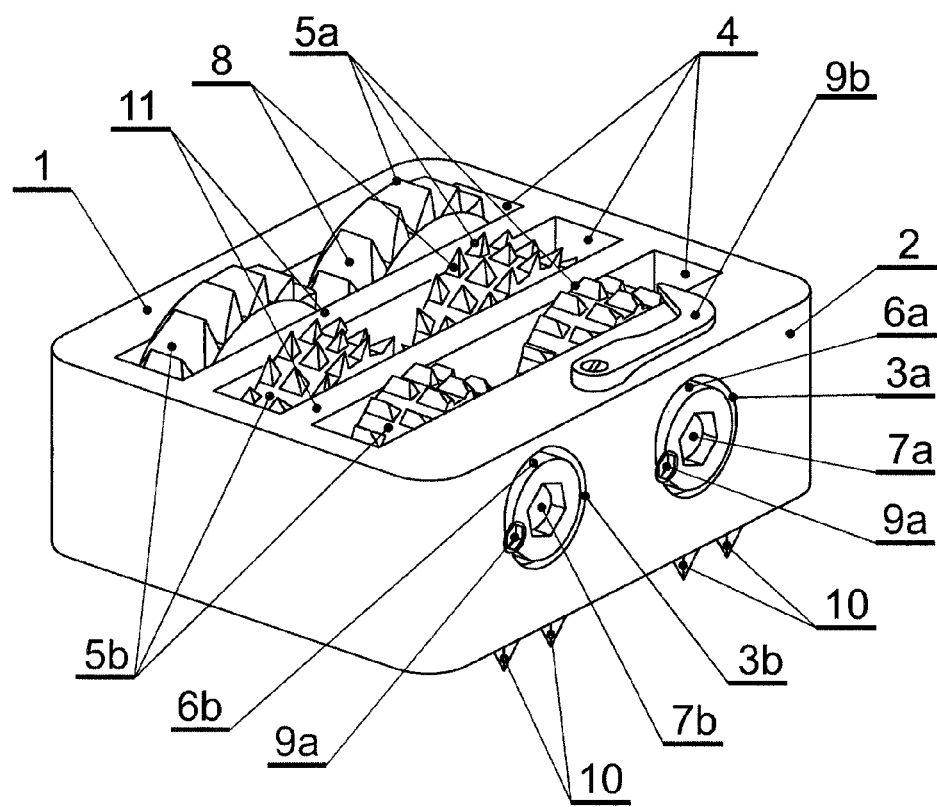
Figure 14:
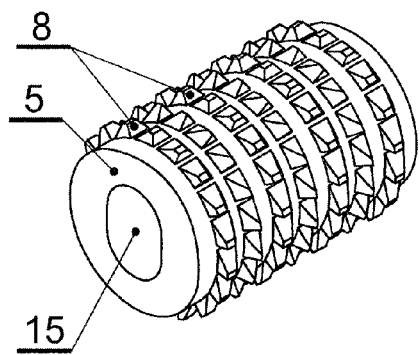
Figure 15:
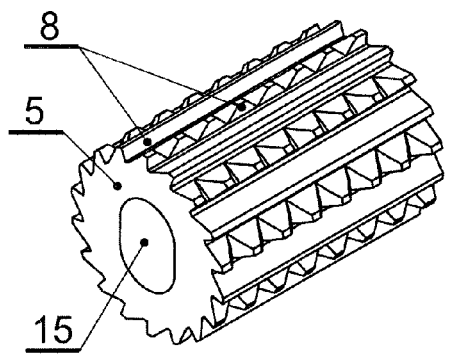
Figure 16:
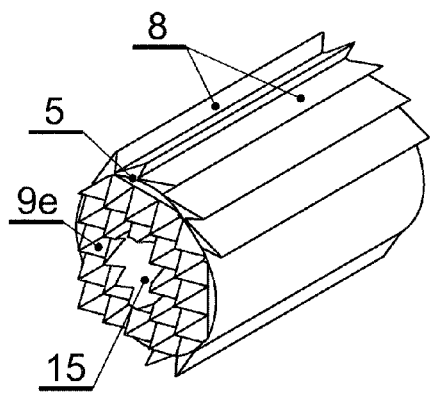
Figure 17:
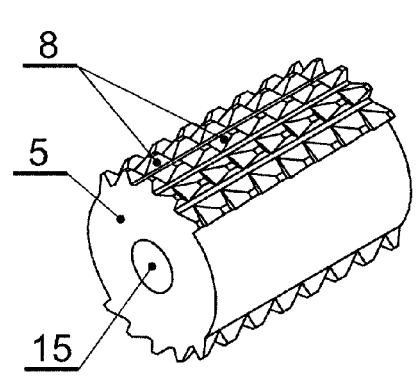
Figure 18:
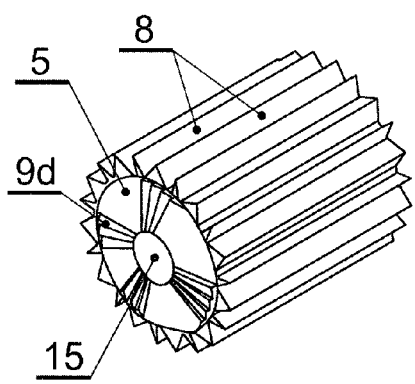
Figure 19:
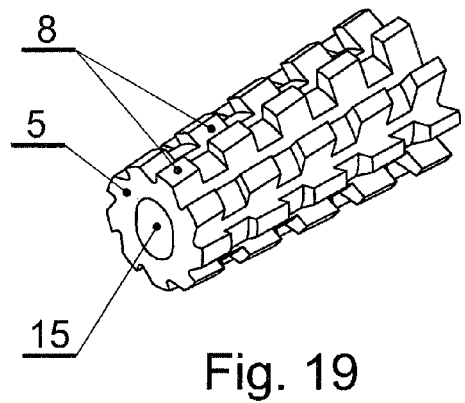
Figure 20:
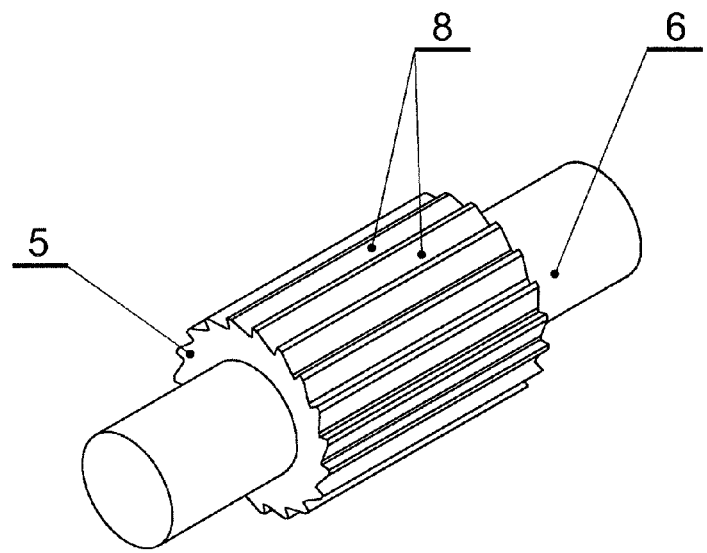
Figure 21:
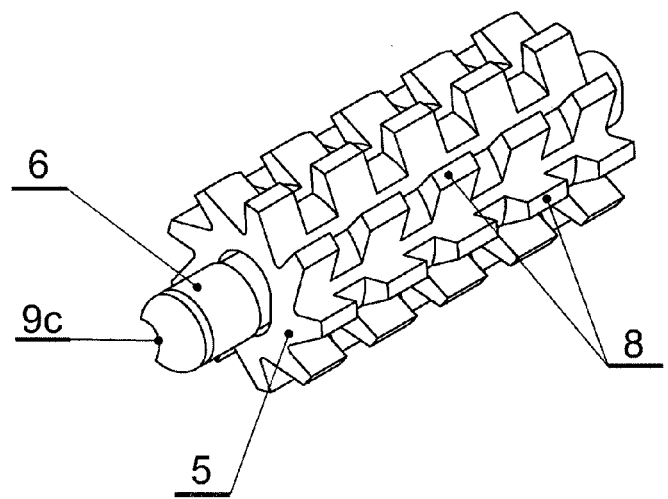
Figure 22:
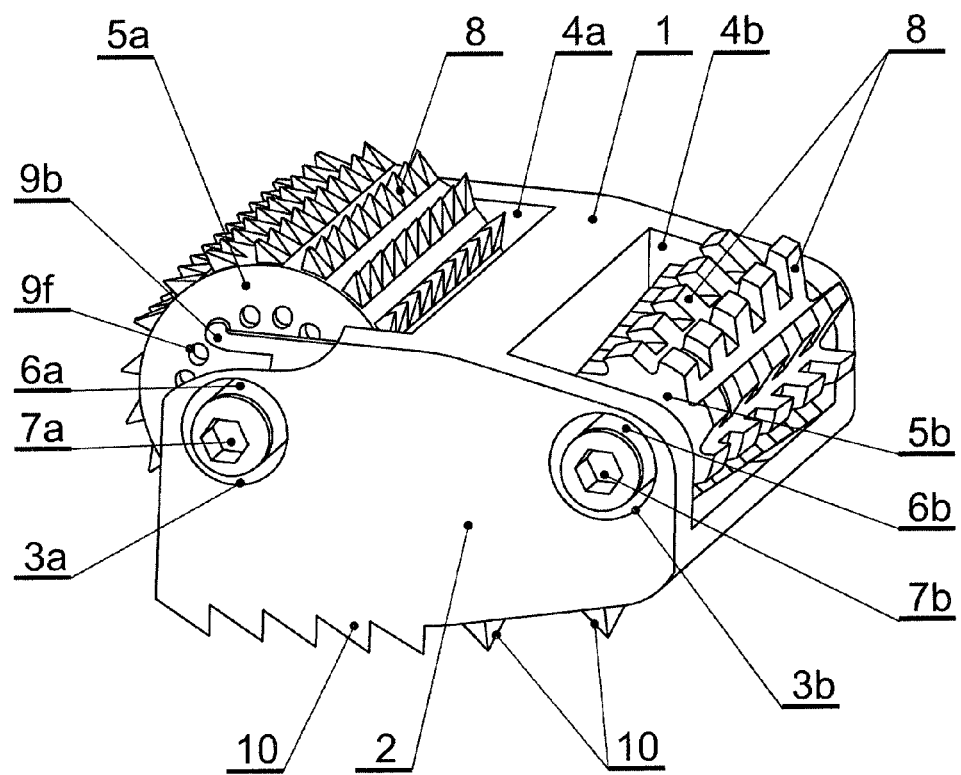
Figure 23:
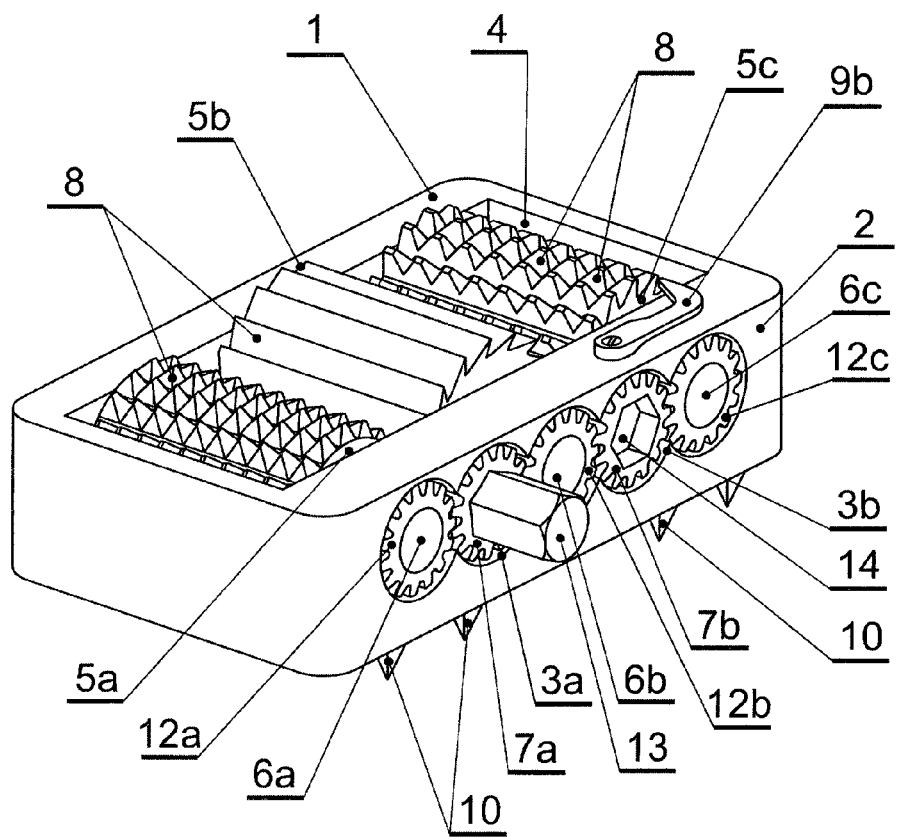
Figure 24:
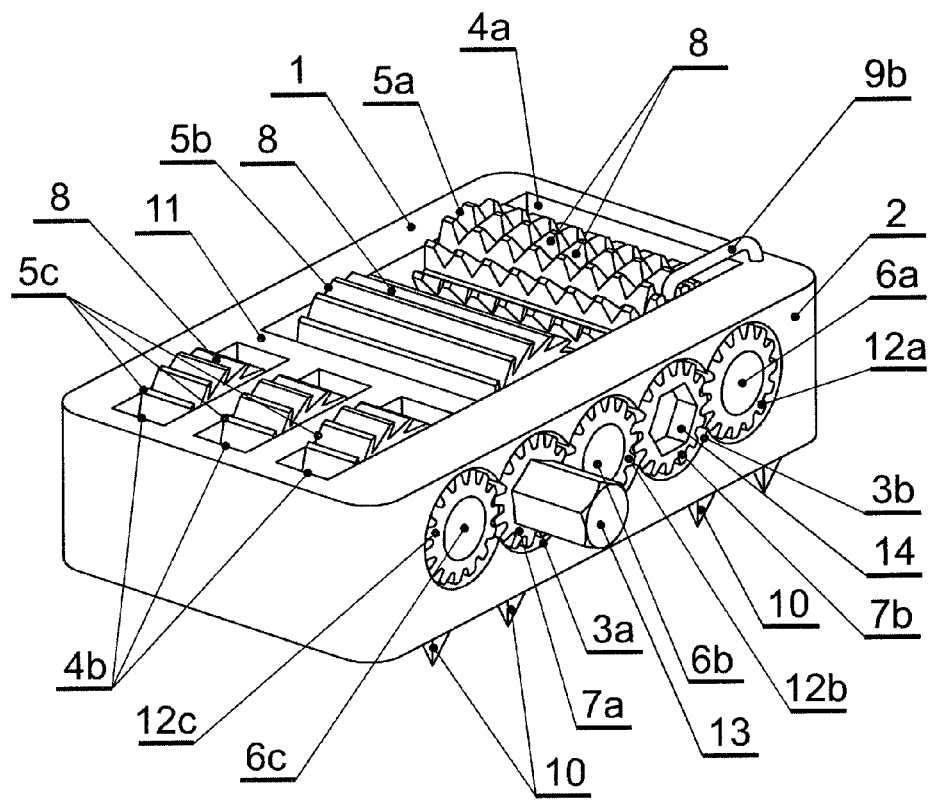
Figure 25:
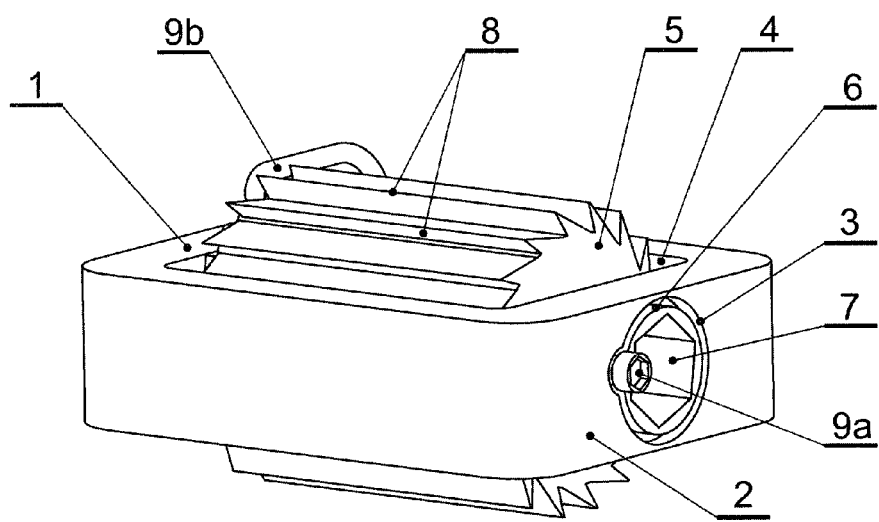
Figure 29:
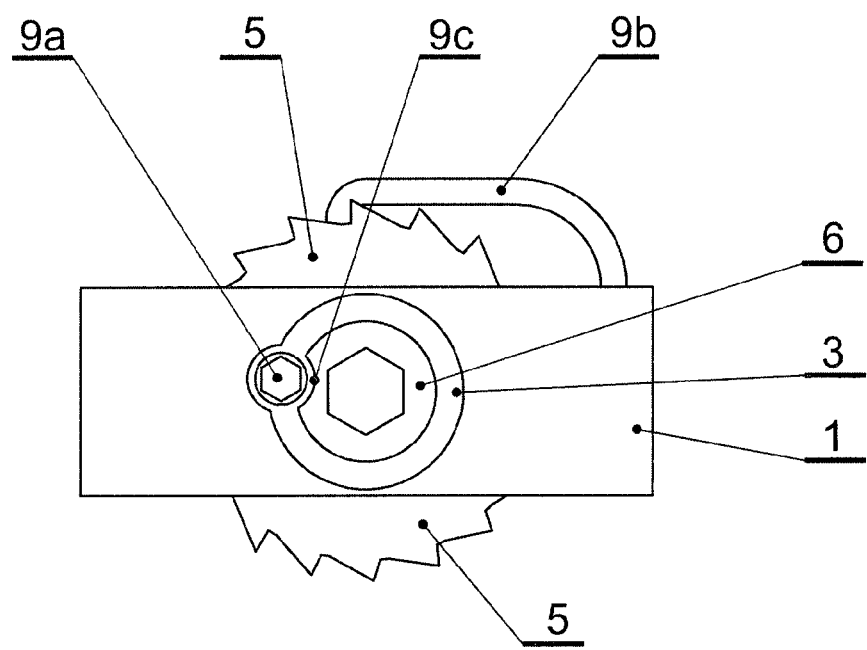
Figure 30:
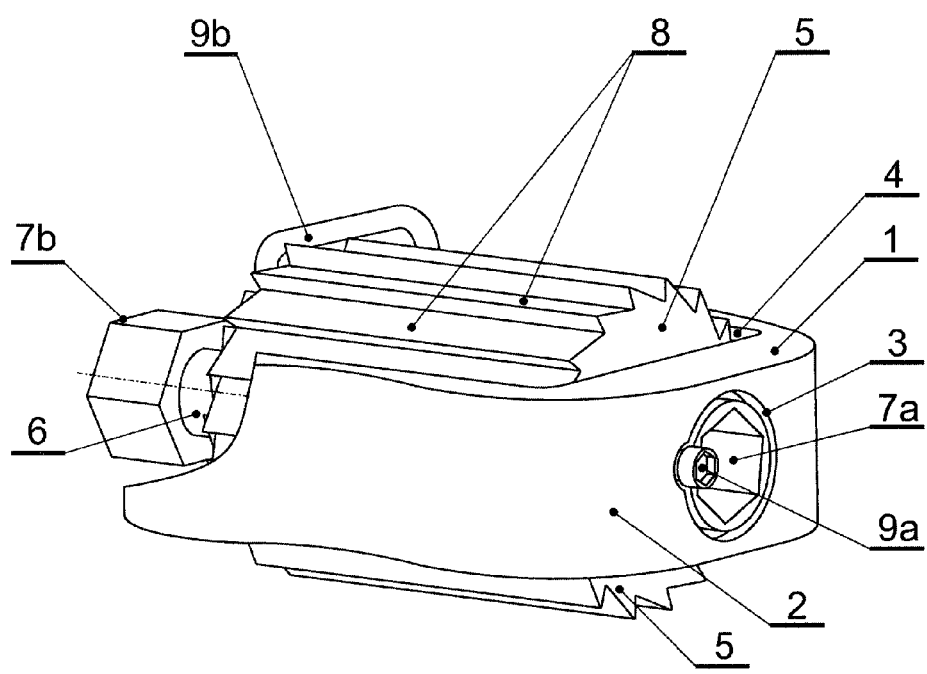
Figure 31:
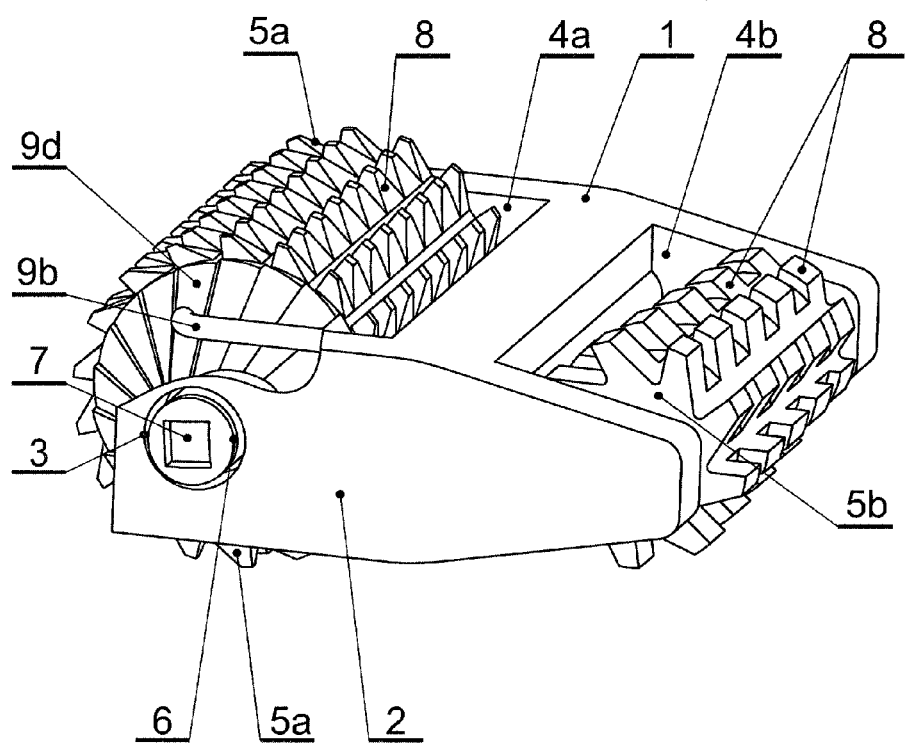
Figure 32:
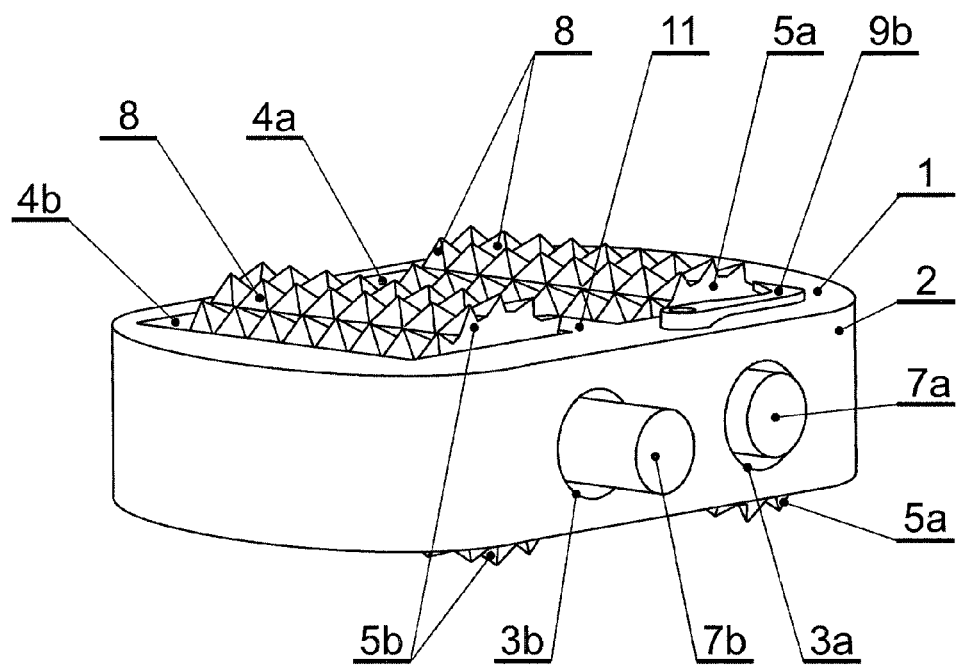
Figure 33:
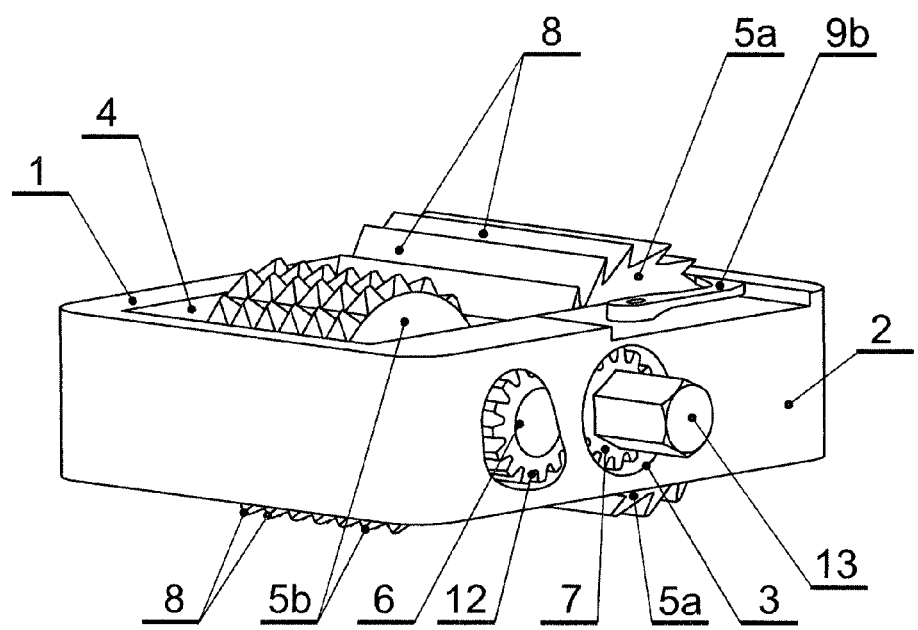
Figure 34:
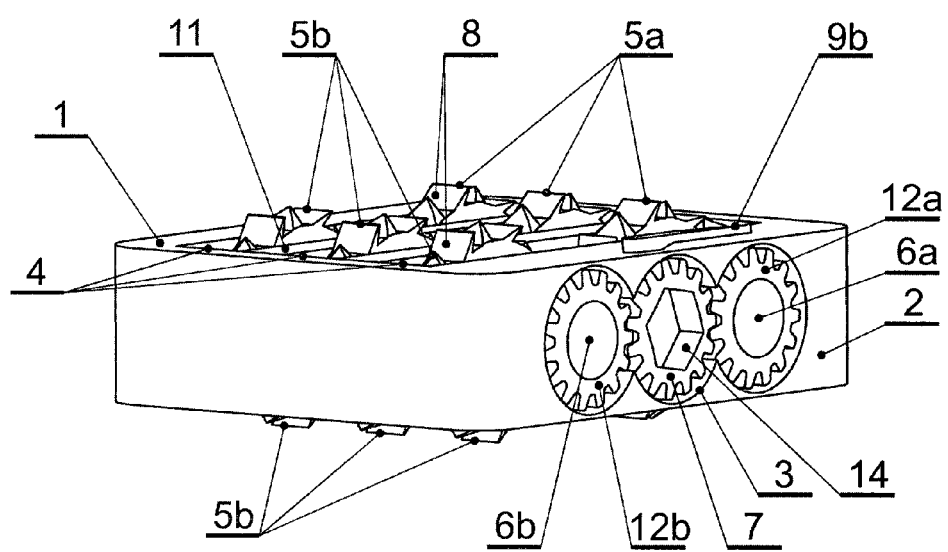
Figure 35:
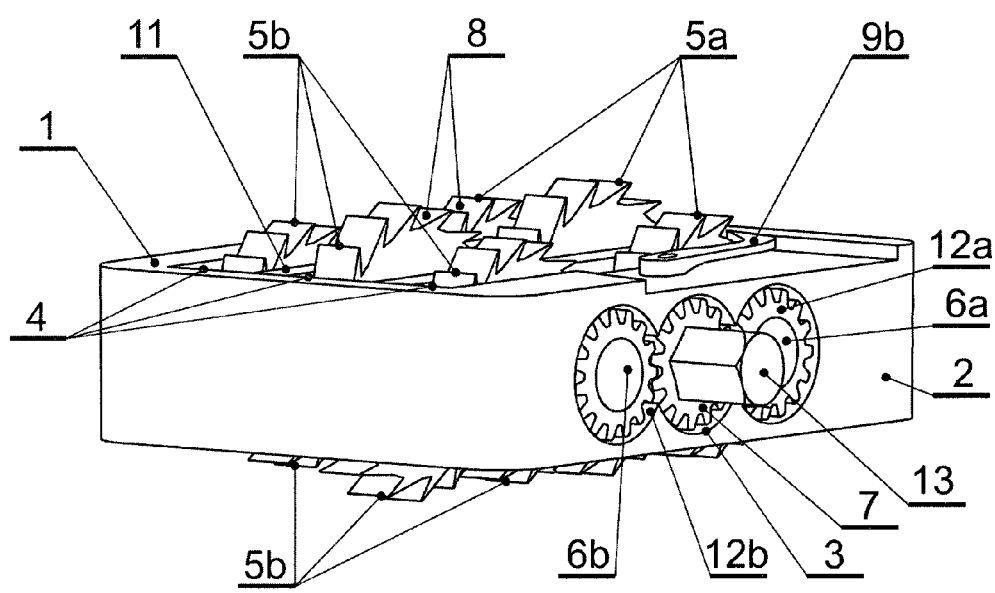
Figure 36:
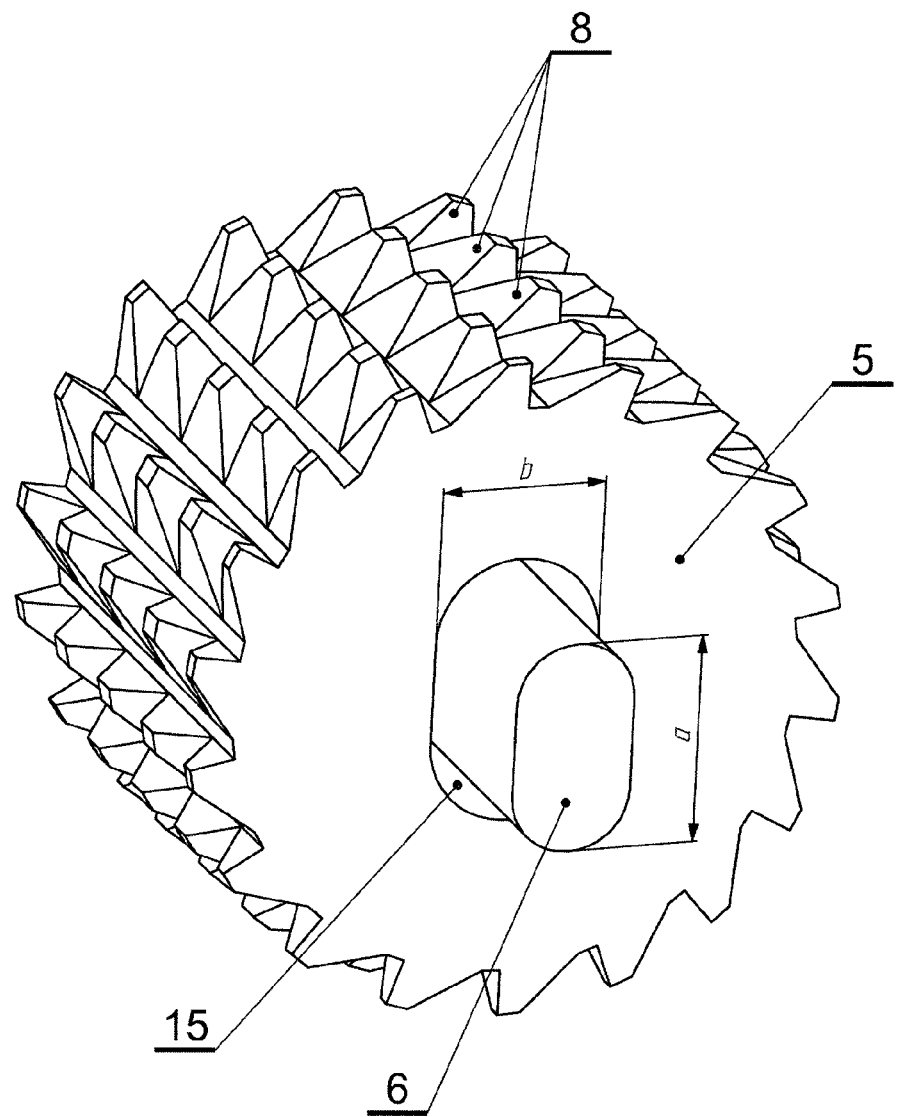
Figure 37:
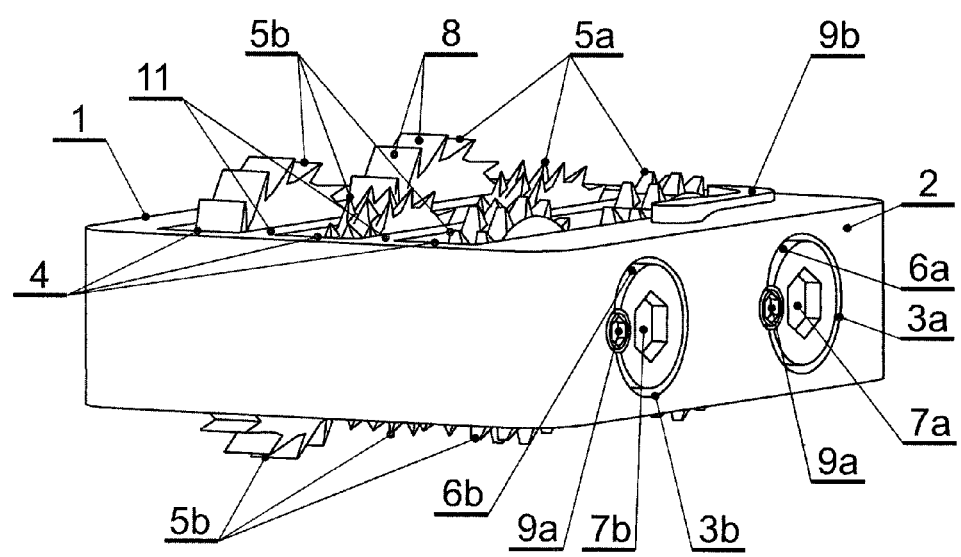
Figure 38:
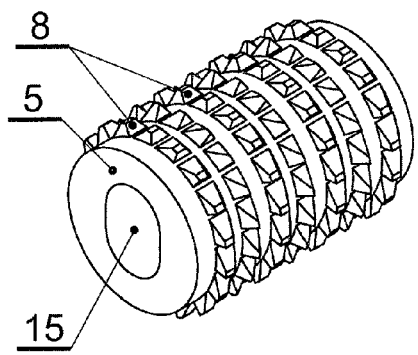
Figure 39:
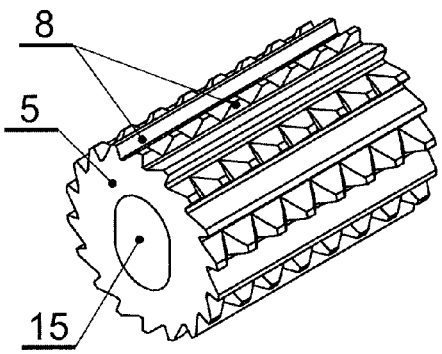
Figure 40:
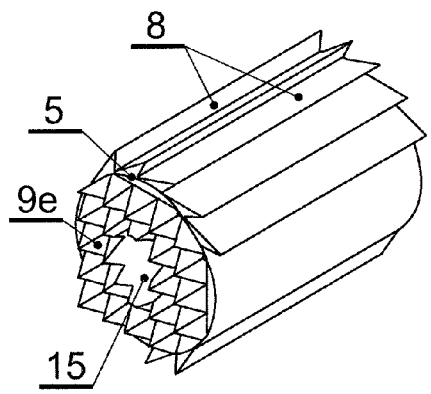
Figure 41:
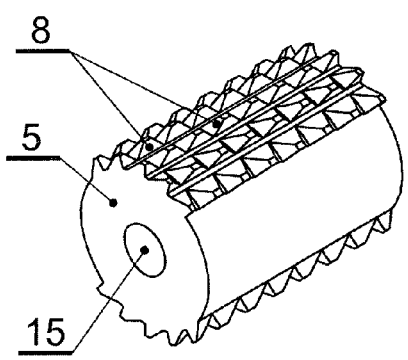
Figure 42:
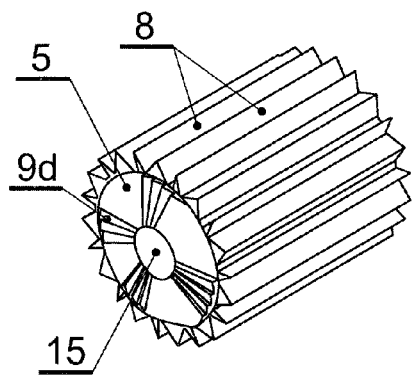
Figure 43:
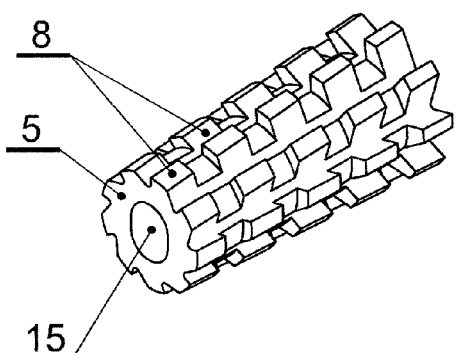
Figure 44:
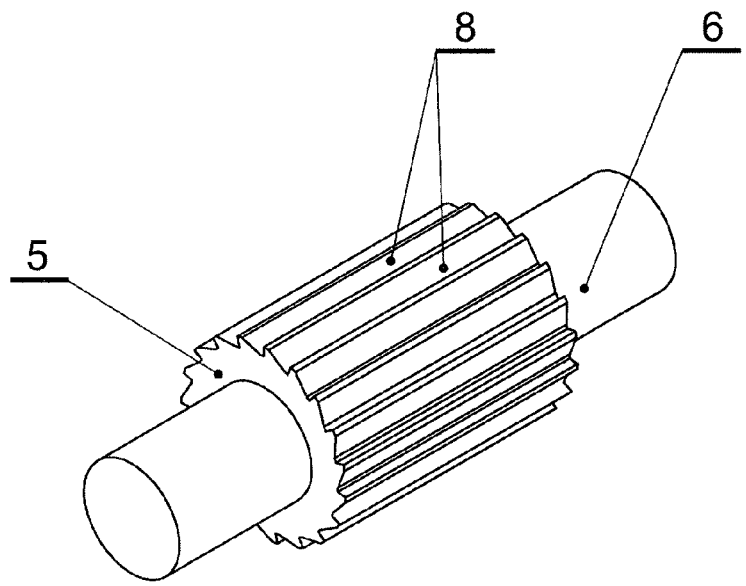
Figure 45:
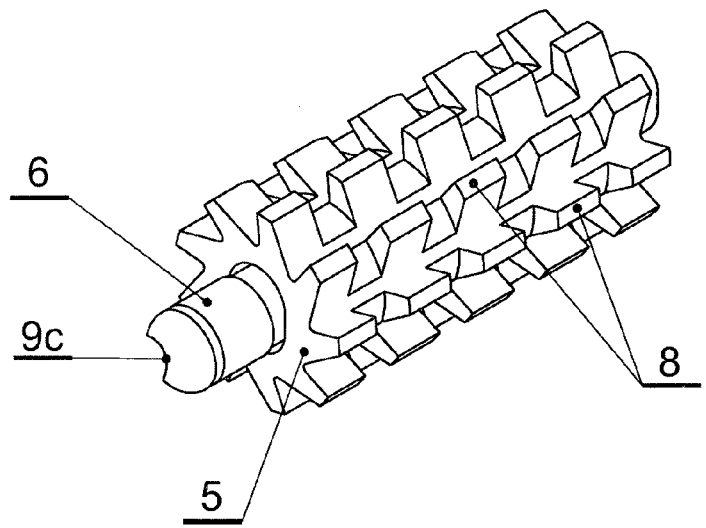
Figure 46:
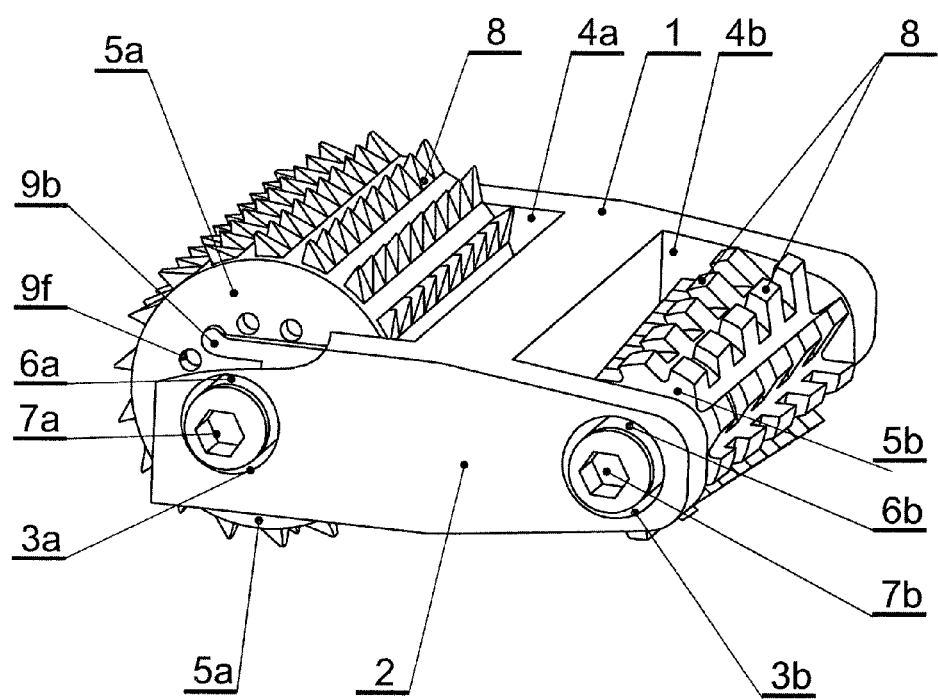
Figure 47:
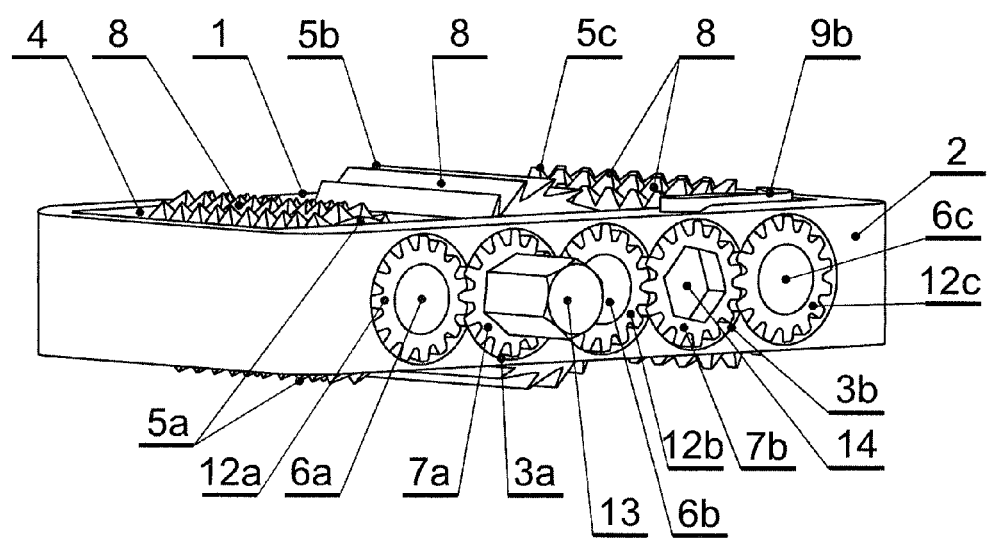
Figure 48:
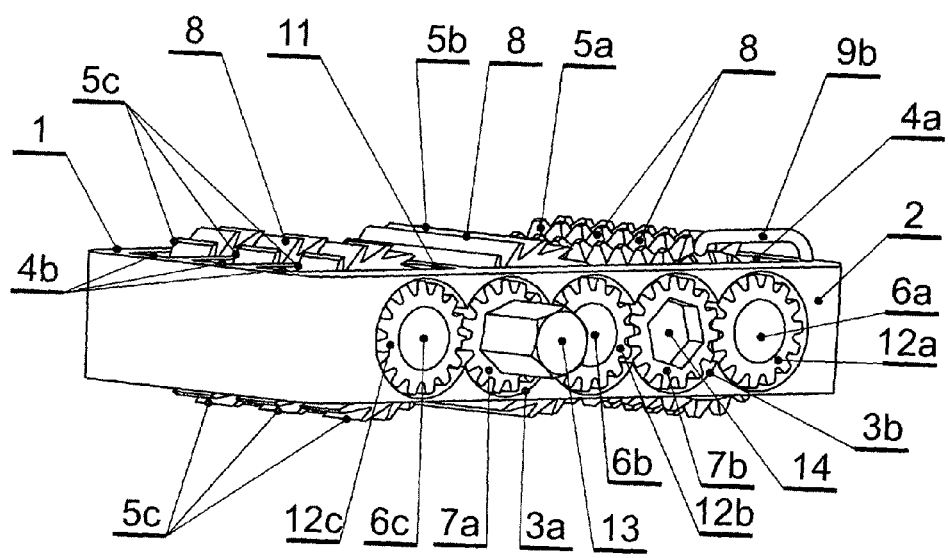

FIG. 10 illustrates a sixth embodiment of an intervertebral implant, with the implant having two rotational elements that each include three separate parts situated in sections of the seat and mounted in a cover, with the cover being in a rectangular shape, where anchoring of the cover is operable to engage a vertebra, and one connecting element in a form of a gear situated within the diameter of the manipulative hole of the cover;

FIG. 11 illustrates a seventh embodiment of an intervertebral implant, with the implant having two rotational elements that each include three separate parts situated in sections of the seat and mounted in a cover, with the cover having a generally rectangular shape, and where anchoring of the cover is operable to engage a vertebra, and one connecting element situated within the diameter of the manipulative hole of the cover;

FIG. 12 depicts a rotational element with a separately fixed axis;

FIG. 13 illustrates an eighth embodiment of an intervertebral implant, with the implant having two rotational elements that each include three separate parts situated in sections of the seat and mounted in a cover, with the cover being in a rectangular shape, where anchoring of the cover is operable to engage a vertebra, and two connecting elements situated within the diameter of two manipulative holes of the cover;

FIG. 14 illustrates another embodiment of a rotational element, with the rotational element including a hole and anchoring latches;

FIG. 15 illustrates another embodiment of a rotational element, with the rotational element including a hole and anchoring latches;

FIG. 16 illustrates another embodiment of a rotational element, with the rotational element including a hole and anchoring latches;

FIG. 17 illustrates another embodiment of a rotational element, with the rotational element including a hole and anchoring latches;

FIG. 18 illustrates another embodiment of a rotational element, with the rotational element including a hole and anchoring latches;

FIG. 19 illustrates another embodiment of a rotational element, with the rotational element including a hole and anchoring latches;

FIG. 20 illustrates another embodiment of a rotational element, with the rotational element including an axis and anchoring latches;

FIG. 21 illustrates another embodiment of a rotational element, with the rotational element including an axis and anchoring latches;

FIG. 22 illustrates a ninth embodiment of an intervertebral implant, with the implant having two rotational elements mounted in a cover, with the cover being in an irregular shape, where anchoring of the cover is operable to engage a vertebra, and two connecting elements, FIG. 23 illustrates a tenth embodiment of an intervertebral implant, with the implant having three rotational elements mounted in a cover, with the cover being in a rectangular shape, where anchoring of the cover is operable to engage a vertebra, and two connecting elements in a gear-shaped form;

FIG. 24 illustrates an eleventh embodiment of an intervertebral implant, with the implant having three rotational elements mounted in a cover, with the cover being in a rectangular shape, where anchoring of the cover is operable to engage a vertebra, and two connecting elements in a gear-shaped form;

FIG. 25 illustrates a twelfth embodiment of the intervertebral implant, with the implant being operable for mutual situating of adjacent vertebrae, said implant having a rectangular shaped cover, a rotational element mounted in the cover and having anchoring of the rotational element operable to engage the adjacent vertebrae, and one connecting element;

FIG. 26 illustrates the intervertebral implant shown in FIG. 25, showing a cross-sectional view of the implant located between adjacent vertebrae taken along a sagittal plane, with the implant having one rotational element mounted in a cover, where anchoring of the rotational element engages the adjacent vertebrae;

FIG. 27 illustrates a perspective view of one of the vertebrae and the intervertebral implant shown in FIG. 26, showing the implant extending relative to the vertebra along the saggital plane;

FIG. 28 illustrates the vertebra and the intervertebral implant similar to FIG. 27, but showing the implant extending relative to the vertebra along a coronal plane;

FIG. 29 illustrates a side elevation of the intervertebral implant shown in FIGS. 25-28, showing an axis of the rotational element defining a recess and a pin situated within the diameter of a manipulative hole of the cover;

FIG. 30 illustrates a thirteenth embodiment of an intervertebral implant, with the implant having one rotational element in mounted in a rectangular shaped cover, with the cover presenting a shape close to the shape of a vertebral body, where anchoring of the rotational element is operable to engage adjacent vertebrae, and two connecting elements;

FIG. 31 illustrates a fourteenth embodiment of an intervertebral implant, with the implant having two rotational elements mounted in a cover that presents an irregular shape, where anchoring of the rotational elements is operable to engage adjacent vertebrae, and one connecting element situated within the diameter of a manipulative hole of the cover;

FIG. 32 illustrates a fifteenth embodiment of an intervertebral implant, with the implant having two rotational elements situated in sections of a seat, mounted in a rectangular shaped cover, where anchoring of the rotational elements operable to engage adjacent vertebrae, and two connecting elements;

FIG. 33 illustrates a sixteenth embodiment of an intervertebral implant, with the implant having two rotational elements situated in sections of a seat, mounted in a rectangular shaped cover, where anchoring of the rotational elements is operable to engage adjacent vertebrae, and a connecting element;

FIG. 34 illustrates a seventeenth embodiment of an intervertebral implant, with the implant having two rotational elements that each include three separate parts situated in sections of a seat and mounted in a rectangular shaped cover, where anchoring of the rotational elements operable to engage adjacent vertebrae, and one connecting element in a form of a gear situated within the diameter of a manipulative hole of the cover;

FIG. 35 illustrates an eighteenth embodiment of an intervertebral implant, with the implant having two rotational elements that each include three separate parts situated in sections of a seat and mounted in a rectangular shaped cover, where anchoring of the rotational elements is operable to engage adjacent vertebrae, and one connecting element in a form of a gear situated within the diameter of a manipulative hole of the cover;

FIG. 36 illustrates a rotational element with a separately fixed axis;

FIG. 37 illustrates a nineteenth embodiment of an intervertebral implant, with the implant having two rotational elements that each include three separate parts situated in sections of a seat and mounted in a rectangular shaped cover, where anchoring of the rotational elements is operable to engage adjacent vertebrae, and two connecting elements situated within the diameter of two manipulative holes of the cover;

FIG. 38 illustrates another embodiment of a rotational element, with the rotational element including a hole and anchoring latches;

FIG. 39 illustrates another embodiment of a rotational element, with the rotational element including a hole and anchoring latches;

FIG. 40 illustrates another embodiment of a rotational element, with the rotational element including a hole and anchoring latches;

FIG. 41 illustrates another embodiment of a rotational element, with the rotational element including a hole and anchoring latches;

FIG. 42 illustrates another embodiment of a rotational element, with the rotational element including a hole and anchoring latches;

FIG. 43 illustrates another embodiment of a rotational element, with the rotational element including a hole and anchoring latches;

FIG. 44 illustrates another embodiment of a rotational element, with the rotational element including an axis and anchoring latches;

FIG. 45 illustrates another embodiment of a rotational element, with the rotational element including an axis and anchoring latches;

FIG. 46 illustrates a twentieth embodiment of an intervertebral implant, with the implant having two rotational elements mounted in a cover that presents an irregular shape, where anchoring of the rotational elements is operable to engage adjacent vertebrae, and two connecting elements;

FIG. 47 illustrates a twenty-first embodiment of an intervertebral implant, with the implant having three rotational elements mounted in a rectangular shaped cover, where anchoring of the rotational elements is operable to engage adjacent vertebrae, and two connecting elements in a form of gears; and FIG. 48 illustrates a twenty-second embodiment of an intervertebral implant, with the implant having three rotational elements mounted in a rectangular shaped cover, where anchoring of the rotational elements is operable to engage adjacent vertebrae, and two connecting elements in a form of gears.

DETAILED DESCRIPTION OF THE PREFERRED EMBODIMENTS

Figure 1:
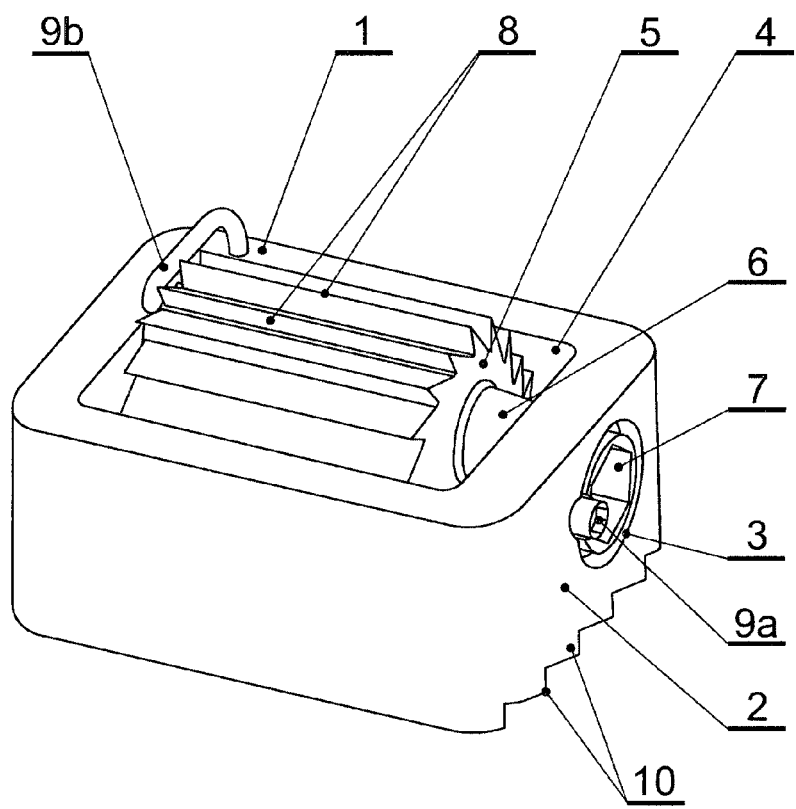
FIG. 1 illustrates an intervertebral implant for mutual situating of adjacent vertebrae having a cover in a rectangular shape, where one anchoring element of the cover is anchored in one of displaced vertebrae and showing the implant including one connecting element.

Presented on FIG. 1 intervertebral implant for mutual situating of adjacent vertebrae contains a cover 1 in a shape close to the rectangle, in which is fixed a driving mechanism. In a lateral wall 2 of the cover 1 a manipulative hole 3 is made. The cover 1 is equipped with one open seat 4. The driving mechanism composes situated in the seat 4 and anchoring in one of displaced vertebrae one rotational element 5 with an axis 6 mounted for an axial movement in lateral walls 2 of the cover 1 perpendicularly to the direction of the displacement of vertebrae against each other, cooperating with the connecting element 7. The rotational element 5 is equipped with anchoring latches 8 projecting over the height of cover's 1 walls 2 from the side contacting with one of displaced vertebrae and anchoring in this vertebrae. Anchoring latches 8 have got a form of paddles of equal dimensions and shapes. The connecting element 7, situated within the diameter of the manipulative hole 3 of the cover 1, cooperates with not visible on the figure separate driving tool. The connecting element 7 constitutes one shaped end of the axis 6 of the rotational element 5. The implant is equipped with two blockades of the rotation of the driving element. One of blockades of the driving mechanism has got a form of a pin 9a situated within the diameter of the manipulative hole 3 of the cover 1 and cooperating with not visible on this figure recess in the axis 6 of the rotational element 5, whereas the second blockade of the rotation constitutes a latch 9b fixed to the cover 1 on the opposite side than the pin 9a, cooperating with the rotational element 5. The lower surface of one of lateral walls 2 of the cover 1 is equipped with anchoring latches 10 in a form of paddles, anchoring in the second of displaced vertebrae.

Figure 2:
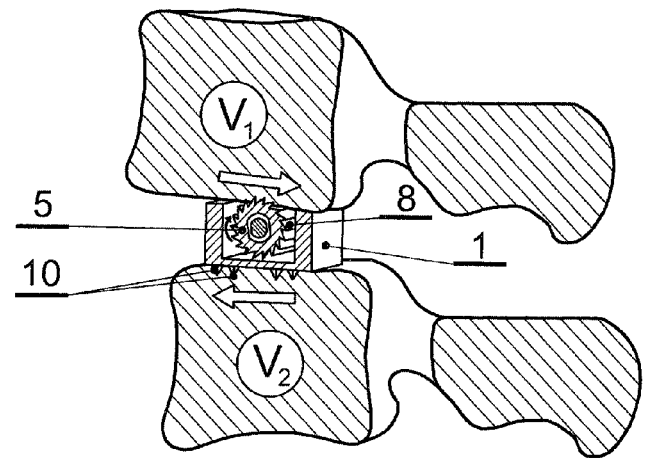
FIG. 2 illustrates the intervertebral implant shown in FIG. 1, showing a cross-sectional view of the implant located between adjacent vertebrae taken along a sagittal plane, with the implant having one rotational element mounted in a cover, and anchoring of the cover in one of displaced vertebrae.

FIG. 2 illustrates graphically the displacement of vertebrae V1 and V2 using situated between them intervertebral implant, having one rotational element 5 fixed in the cover 1. Anchoring latches 8 of the rotational element 5 project over the height of walls 2 of the cover 1 from the side contacting with one of displaced vertebrae V1 and anchor in this vertebra V1, whereas anchoring projections 10 fixed to the cover 1 of the implant anchor in the second vertebra V2.

Figures 3, 4:
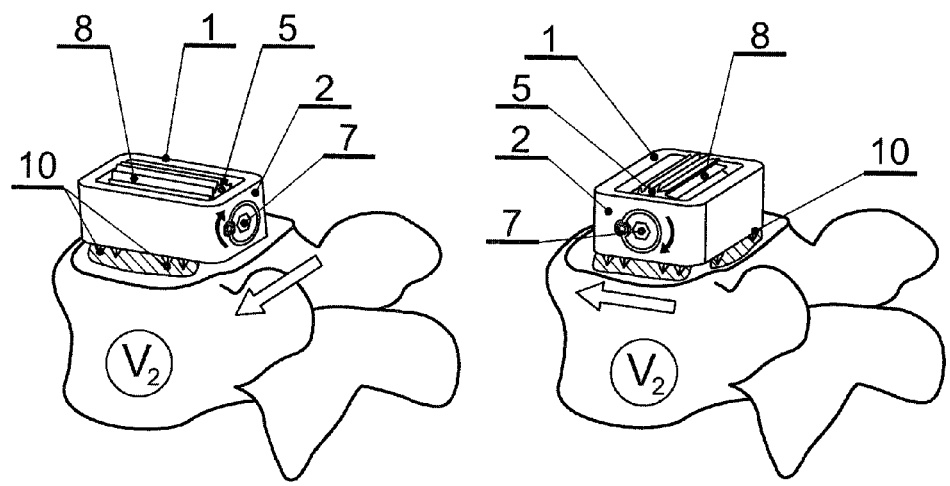
FIG. 3 illustrates a perspective view of one of the vertebrae and the intervertebral implant shown in FIG. 2 showing the implant extending relative to the vertebra along the saggital plane.
FIG. 4 illustrates the vertebra and the intervertebral implant similar to FIG. 3, but showing the implant extending relative to the vertebra along a coronal plane.

On FIG. 3 is illustrated graphically the displacement of vertebrae in the coronal plane using intervertebral implant, having fixed in the cover 1 one rotational element 5 and one connecting element 7. The cover is equipped with anchoring projections 10 anchoring in one of displaced vertebrae V2. Anchoring latches 8 of the rotational element 5 project over the height of walls 2 of the cover 1 and anchor in not visible on the figure second vertebra, which is displaced by the movement of the rotational element 5. The movement of displaced vertebra takes place in the relation to the vertebra V2 and the cover 1, which is held in the immobile position as a result of anchoring of anchoring projections 10 in the second vertebra V2.

On FIG. 4 is illustrated graphically the displacement of vertebrae in the sagittal plane using an intervertebral implant, having one rotational element 5 and one connecting element 7 fixed in the cover 1. The cover 1 is equipped with anchoring projections 10 anchoring in one of displaced vertebrae V2. Anchoring latches 8 of the rotational element 5 project over the height of walls 2 of the cover 1 and anchor in not visible on the figure second vertebra, which is displaced by the movement of the rotational element 5. The movement of displaced vertebra takes place in the relation to the vertebra V2 and the cover 1, which is held in the immobile position as a result of anchoring of anchoring projections 10 in the second vertebra V2.

Figure 5:
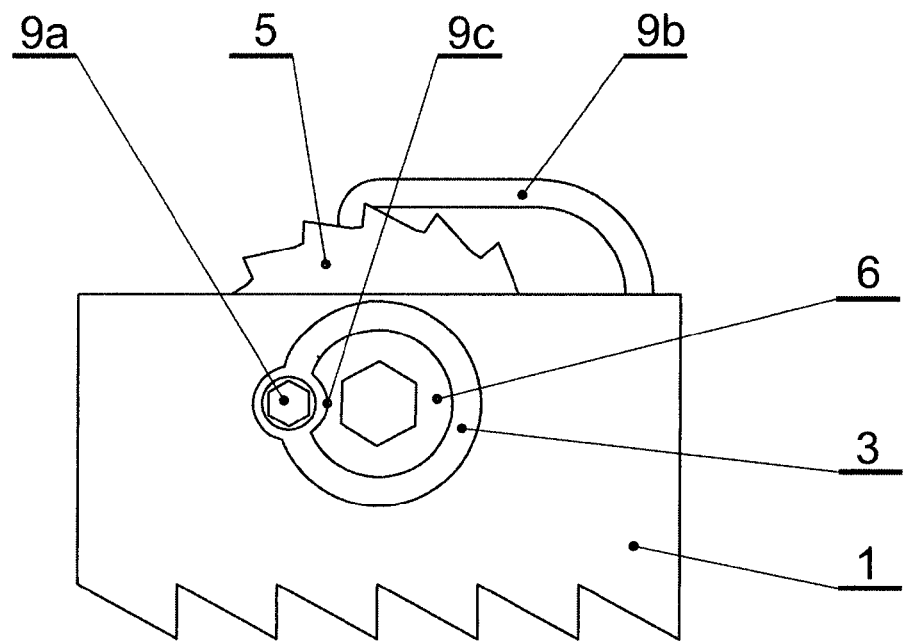
FIG. 5 illustrates a side elevation of the intervertebral implant shown in FIGS. 1-4, showing an axis of the rotational element defining a recess and a pin situated within the manipulative hole of a cover.

FIG. 5 illustrates two blockades of the rotation—one in a form of a latch 9b fixed to the cover 1, cooperating with the rotational element 5 and the second in a form of a pin 9a situated within the diameter of the manipulative hole 3 of the cover 1, cooperating with the recess 9c in the axis 6 of the rotational element 5.

Figure 6:
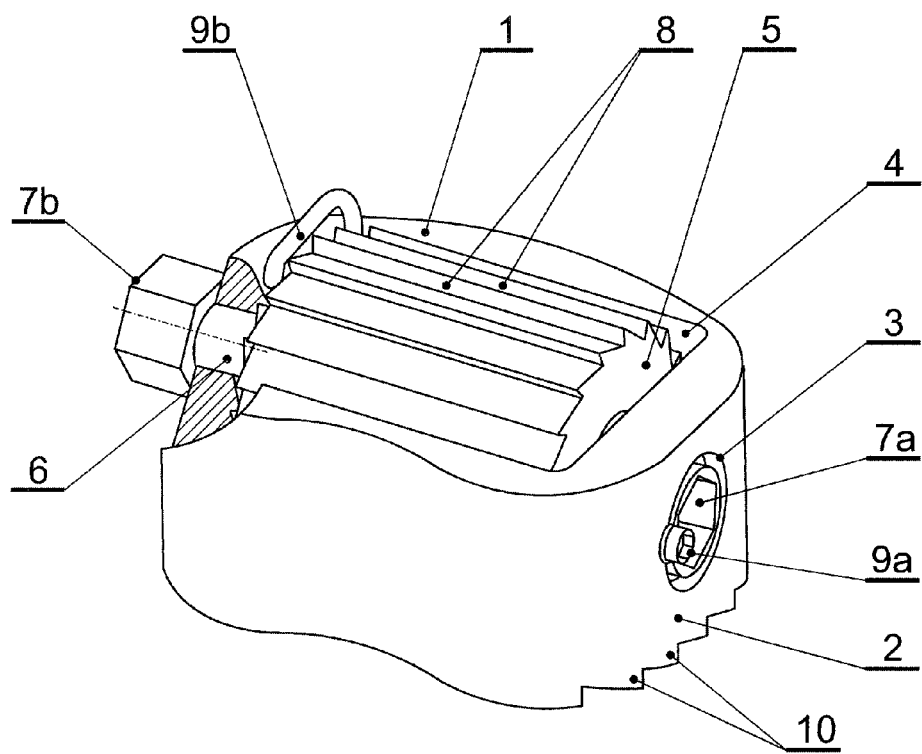
FIG. 6 illustrates a second embodiment of the intervertebral implant having one rotational element mounted in a cover, with the cover presenting a shape close to the shape of the vertebral body, where anchoring of the cover is operable to engage a vertebra, and two connecting elements.

In an embodiment illustrated on FIG. 6 the cover 1 in a shape close to the shape of vertebral body is equipped with two manipulative holes 3 situated symmetrically in lateral walls 2 of the cover 1. Situated in the seat 4 of the cover 1 one rotational element 5 with an axis mounted for axial movement in lateral walls 2 of the cover 1 perpendicularly to the direction of the displacement of vertebrae in the relation to each other is equipped with anchoring latches 8, projecting over the height of walls 2 of the cover 1 from the side contacting with one of displaced vertebrae and anchoring in this vertebra. The rotational element 5 cooperates with two connecting elements 7a, 7b. Each of connecting elements 7a, 7b is situated within the diameter of the manipulative hole 3 of the cover 1 and cooperates with not visible on the figure separate driving tool. Each connecting element 7a, 7b composes shaped end of the axis 6 of the rotational element 5, whereby one connecting element 7b has got a form of a shaped element with a hexagonal cross section. This constructional variant allows driving the driving element 5 using one of connecting elements 7a, 7b or both simultaneously, depending on the operating field. The implant is provided with two blockades of the rotation of the driving mechanism. One of the blockades of the rotation of the driving mechanism has got a form of a pin 9a situated within the diameter of the manipulative hole 3 of the cover 1 and cooperating with not visible on this figure recess in the axis 6 of the rotational element 5, whereas the second blockade of the rotation constitutes a latch 9b fixed to the cover 1 at the opposite side than the pin 9a, cooperating with the rotational element 5. The lower surface of the one of lateral walls 2 of the cover 1 is equipped with anchoring latches 10 in a form of paddles, anchoring in the second of displaced vertebrae.

Figure 7:
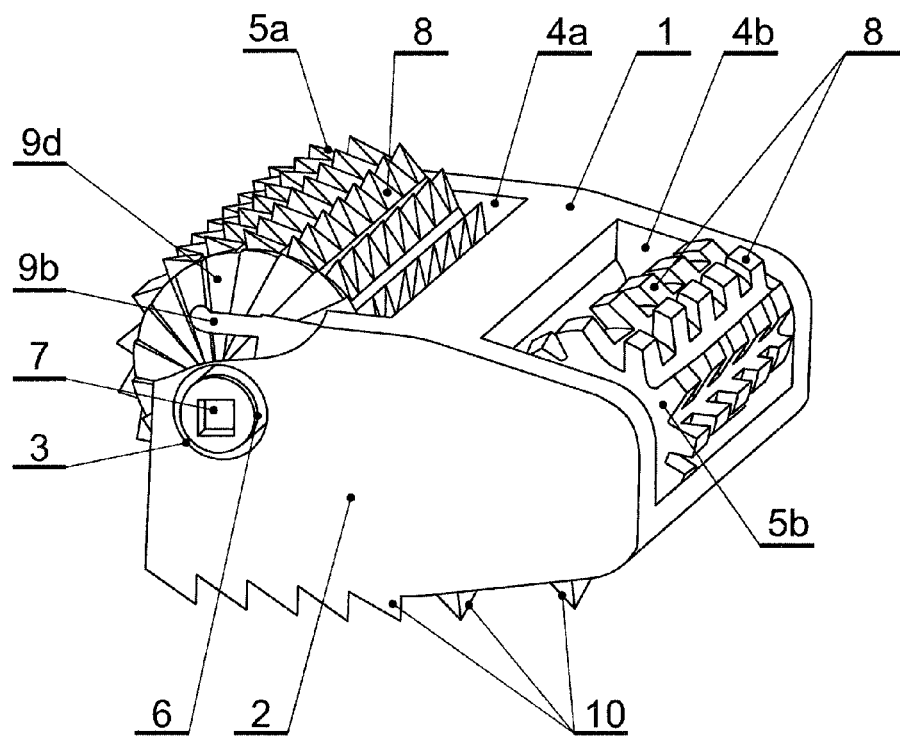
FIG. 7 illustrates a third embodiment of an intervertebral implant, with the implant having two rotational elements mounted in a cover, where anchoring of the cover is operable to engage a vertebra, and one connecting element situated within the diameter of the manipulative hole of the cover.

In an embodiment of the invention illustrated on FIG. 7, the cover 1 has got a form of a frame of an irregular shape provided with one manipulative hole 3. The cover 1 is equipped with two open seats 4a, 4b, in which are situated two rotational elements 5a, 5b of the driving mechanism of various dimensions, separated from each other with a fragment of the cover 1, provided with anchoring latches 8 projecting over the height of walls 2 of the cover 1 from the side contacting with one of displaced vertebrae and anchoring in this vertebra. The axis 6 of each rotational element 5a, 5b is mounted for an axial movement in the cover 1 perpendicularly to the direction of the displacement of vertebrae according to each other. One rotational element 5a cooperates with the connecting element 7 and is provided with anchoring latches 8 in a form of spikes of equal dimensions. The second rotational element 5b, on the other hand, is equipped with anchoring latches 8 in a form of teeth with a shape close to rectangles of equal dimensions. The connecting element 7 is situated within the diameter of the manipulative hole 3 of the cover 1 and composes a shaped end of the axis 6 of one of rotational elements 5a. The connecting element cooperates with not visible on the figure separate driving tool. The blockade of the rotation of the driving mechanism has got a form of paddles 9d situated on the lateral surface of the rotational element 5a, cooperating with one latch 9b fixed to the lateral wall 2 of the cover 1. The lower surface of one of lateral walls 2 of the cover 1 is equipped with anchoring latches 10 in a form of paddles and spikes, anchoring in the second of displaced vertebrae.

Figure 8:
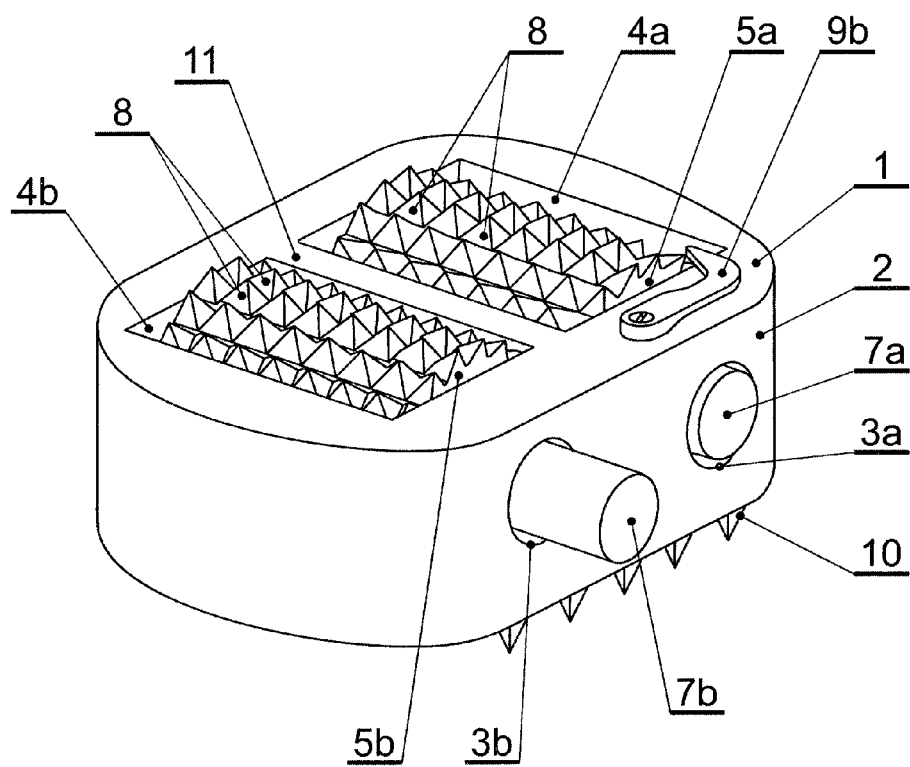
FIG. 8 illustrates a fourth embodiment of an intervertebral implant, with the implant having two rotational elements mounted in a cover, and where anchoring of the cover is operable to engage a vertebra, and two connecting elements.

In an embodiment of the invention illustrated in FIG. 8 the intervertebral implant for mutual situating of adjacent vertebrae has got a driving mechanism fixed in the cover 1 with a cross section close to an oval, provided with two manipulative holes 3a, 3b, situated in the same lateral wall 2 of the cover 1. The cover 1 is equipped with two separated from each other with the separating wall 11 open seats 4a, 4b, in which are situated two rotational elements 5a, 5b of the driving mechanism of equal dimensions and shapes, provided with anchoring latches 8 projecting over the height of walls 2 of the cover 1 from the side contacting with one of displaced vertebrae and anchoring in this vertebra. Anchoring latches 8 of each rotational element 5a, 5b have got a form of spikes of equal dimensions and shapes. In each manipulative hole 3a, 3b is situated one connecting element 7a, 7b, composing one end of the axis of each rotational element 5a, 5b, with various length. Each of connecting elements 7a, 7b cooperates with not visible on the figure separate driving tool. Such constructional variant enables driving of rotational elements 5a, 5b using one of connecting elements 7a, 7b or both simultaneously, depending on the operating field. The blockade of the rotation of the driving element has got a form of the latch 9b fixed to the lateral wall 2 of the cover 1, cooperating with one rotational element 5a. Lower surface of one of lateral walls 2 of the cover 1 is equipped with anchoring latches 10 in a form of spikes, anchoring in the second of displaced vertebrae.

Figure 9:
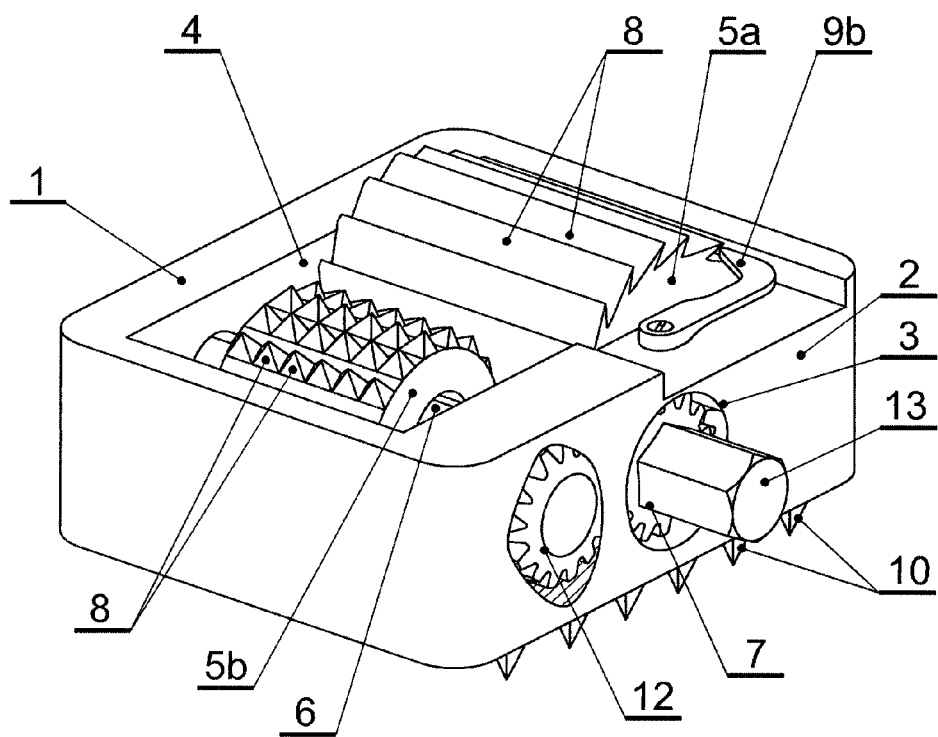
FIG. 9 illustrates a fifth embodiment of an intervertebral implant, with the implant having two rotational elements mounted in a cover, where anchoring of the cover is operable to engage a vertebra, and a connecting element.

In one embodiment of the invention illustrated on FIG. 9 the cover 1 in a shape close to the rectangle is equipped with one manipulative hole 3 and one open seat 4, in which are situated separated from each other two rotational elements 5a, 5b of the driving mechanism. Rotational elements 5a, 5b have various dimensions and are equipped with anchoring latches 8 projecting over the height of walls 2 of the cover 1 from the side contacting with one of displaced vertebrae and anchoring in this vertebra. One rotational element 5a is equipped with anchoring latches 8 in a form of paddles of equal dimensions and shapes, whereas the second rotational element 5b is equipped with anchoring latches 8 in a form of spikes of equal dimensions and shapes, situated on a part of the external surface of this rotational element 5b. The axis 6 of the second rotational element 5b composes its separable part, and on its end, situated from the side of the manipulative hole 3, a gear 12 is seated, fixed in the cover 1. The driving mechanism has got one connecting element 7 situated in the manipulative hole 3 of the cover 1, having a form of a gear cooperating with the gear 12 seated on selected end of the axis 6 of one rotational element 5b. The connecting element 7 is equipped with the plug 13. The blockade of the rotational mechanism has got a form of a latch 9b fixed to the lateral wall 2 of the cover 1, cooperating with one rotational element 5a. The lower surface of one of lateral walls 2 of the cover 1 is equipped with anchoring projections 10 in a form of spikes, anchoring in the second of displaced vertebrae. In an embodiment of the invention illustrated on FIG. 10 the cover 1 is equipped with one manipulative hole 3 and one open seat divided on three sections separated from each other with separating walls 11. Each of two rotational elements 5a, 5b is made of seated on a common axis 6a, 6b three separate parts of equal dimensions, situated in corresponding to them, separated with separating walls 11 sections of the seat 4. Each separate part of each rotational element 5a, 5b is equipped with anchoring latches 8 in a form of teeth and spikes of various shapes and dimensions, projecting over the height of the walls 2 of the cover 1 from the side contacting with one of displaced vertebrae and anchoring in this vertebra. On one end of the axis 6a, 6b of each rotational element 5a, 5b, situated from the side of manipulative hole 3, a gear 12a, 12b is seated, fixed in the cover 1. The connecting element 7 is situated in the manipulative hole 3 of the cover 1 and cooperates with not visible on the figure separate driving tool. The connecting element 7 has got a form of a gear provided with a recess 14, cooperating with gears 12a, 12b composing selected ends of the axis 6a, 6b of each rotational element 5a, 5b, seated on its both sides. The blockade of the rotation of the driving mechanism has got a form of one latch 9b fixed to the lateral wall 2 of the cover 1, cooperating with one rotational element 5a. Lower surface of one of lateral walls 2 of the cover 1 is equipped with anchoring projections 10 in a form of spikes and teeth, anchoring in the second of displaced vertebrae.

In an embodiment of the invention illustrated on FIG. 11 each of two rotational elements 5a, 5b is made of seated on a common axis 6a, 6b three separate parts of various dimensions, placed in corresponding to them, separated with separating walls 11 sections of the seat 4, and each separate part of each rotational element 5a, 5b is equipped with anchoring latches 8 in a form of paddles of equal dimensions, projecting over the height of walls 2 of the cover 1 from the side contacting with one of displaced vertebrae and anchoring in this vertebra. On one end of the axis 6a, 6b of each rotational element 5a, 5b, situated from the side of the manipulative hole 3, a gear 12a, 12b is seated, fixed in the cover 1. The connecting element 7 is situated in the manipulative hole 3 of the cover 1 and cooperates with not visible on the figure separate driving tool. The connecting element 7 has got a form of a gear cooperating with gears 12a, 12b constituting selected ends of the axis 6a, 6b of each rotational element 5a, 5b, seated on its both sides and is equipped with a plug 13. The blockade of the rotation of the driving mechanism has got a form of one latch 9b fixed to the lateral wall 2 of the cover 1, cooperating with one rotational element 5a. The lower surface of one of lateral walls 2 of the cover 1 is equipped with anchoring projections 10 in a form of spikes and teeth, anchoring in the second of displaced vertebrae.

Showed on a FIG. 12 rotational element 5 is equipped with anchoring latches 8 in a form of spikes of equal dimensions and shapes. Shaped axis 6 of the rotational element 5 constitutes its separable part, and the greatest dimension A of the cross section of the axis 6 is greater than the transverse dimension B of the hole 15 of the rotational element 5.

In an embodiment illustrated on FIG. 13 the cover 1 is provided with two manipulative holes 3a, 3b situated in the same lateral wall 2 of the cover 1 and one open seat 4 divided on three sections. In the seat 4 are placed two rotational elements 5a, 5b separated from each other. Each rotational element 5a, 5b is made of seated on a common axis 6a, 6b three separate parts of various dimensions, placed in corresponding to them, separated with separating walls 11 sections of the seat 4. Separate parts of each rotational element 5a, 5b are equipped with anchoring latches 8 with various dimensions and shapes of paddles, spikes and teeth. Anchoring latches 8 of rotational elements 5a, 5b project over the height of walls 2 of the cover 1 from the side contacting with one of displaced vertebrae and anchor in this vertebra. The implant is equipped with two connecting elements 7a, 7b. Each connecting element 7a, 7b composes one shaped end of the axis 6a, 6b of each rotational element 5a, 5b, situated in one manipulative hole 3a, 3b of the cover 1. The implant is equipped with three blockades of the rotation of the driving mechanism. Each of two blockades of the rotation has got a form of a pin 9a situated within the diameter of selected manipulative hole 3a, 3b of the cover 1, cooperating with not visible on the figure recess in the axis 6a, 6b of selected rotational element 5a, 5b. The third blockade of the rotation has got a form of one latch 9b fixed to the cover 1 and cooperating with one rotational element 5a. There is a possibility to drive rotational elements 5a, 5b using one of connecting elements 7a, 7b or two connecting elements 7a, 7b simultaneously, depending on the operating field. The lower surface of one of lateral walls 2 of the cover 1 is equipped with anchoring projections 10 in a form of two pairs of spikes, anchoring in the second of displaced vertebrae.

On FIG. 14-19 are shown various embodiments of rotational elements 5 with anchoring latches 8 and various holes 15.

Illustrated on FIG. 14 rotational element 5 is equipped with a shaped hole 15 and anchoring latches 8 in a form of teeth and spikes of equal dimensions.

Illustrated on FIG. 15 rotational element 5 is equipped with a shaped hole 15 and anchoring latches 8 in a form of teeth and paddles of various dimensions and shapes.

Illustrated on FIG. 16 rotational element 5 is equipped with a shaped hole 15 and anchoring latches 8 in a form of paddles of equal shapes and dimensions. The lateral surface of the rotational element 5 is equipped with teeth 9e, composing element of the blockade of the rotation of the driving mechanism.

Illustrated on FIG. 17 rotational element 5 is equipped with a circular hole 15 and anchoring latches 8 in a form of spikes of equal dimensions, made on a part of the surface of the rotational element 5.

Illustrated on FIG. 18 rotational element 5 is equipped with a round hole 15 and anchoring latches 8 in a form of paddles of various dimensions. The lateral surface of the rotational element 5 is equipped with paddles 9d, constituting elements of the blockade of the rotation of the driving mechanism.

Illustrated on FIG. 19 rotational element 5 has got a conical shape and is equipped with a shaped hole 15 and anchoring latches 8 in a form of teeth of equal shapes and various dimensions.

Illustrated on FIG. 20 rotational element 5 is equipped with anchoring latches 8 in a form of paddles of equal shapes and dimensions. The axis 6 of the rotational element 5 has got a circular shape and constitutes its non-separable part.

Illustrated on FIG. 21 rotational element 5 is equipped with anchoring latches 8 in a form of teeth of equal shapes and dimensions. Shaped axis 6 is fixed in the rotational element 5 separately. In the axis 6 of the rotational element 5 a recess 9c is made.

In an embodiment of the invention illustrated on FIG. 22 the cover 1 has got a form of a frame of irregular shape, equipped with two manipulative holes 3a, 3b situated in the same lateral wall 2 of the cover 1. The cover 1 is equipped with two open seats 4a, 4b, in which are placed separated from each other with a fragment of the cover 1 two rotational elements 5a, 5b of the driving mechanism of various dimensions, cooperating with two connecting elements 7a, 7b. Each rotational element 5a, 5b cooperates with one connecting element 7a, 7b. One rotational element is equipped with anchoring latches 8 in a form of spikes of various dimensions, whereas the second rotational element 5b has got a shape close to a cone narrowing in the direction of (towards) the connecting element 7b and is equipped with anchoring latches 8 in a form of teeth in a shape close to rectangles of various dimensions. Anchoring latches 8 on each rotational element 5a, 5b project over the height of walls 2 of the cover 1 from the side contacting with one of displaced vertebrae and anchor in this vertebra. Each connecting element 7a, 7b is situated within the diameter of the manipulative hole 3a, 3b of the cover 1 and cooperates with not visible on the figure separate driving tool. Each connecting element 7a, 7b constitutes one shaped end of the axis 6a, 6b of each rotational element 5a, 5b. There is a possibility of driving the implant using one of connecting elements 7a, 7b, depending on the operational field. The blockade of the rotation has got a form of holes 9f made on the lateral surface of one rotational element 5a, cooperating with a latch 9b. The latch 9b is fixed to the lateral wall 2 of the cover 1 and cooperates with the rotational element 5a equipped with anchoring latches 8 in a form of teeth in a shape of cones. The lower surface of one of lateral walls 2 of the cover 1 is equipped with anchoring projections 10 in a form of paddles and spikes, anchoring in the second of displaced vertebrae.

In an embodiment of the invention illustrated on FIG. 23 the intervertebral implant for mutual situating of adjacent vertebrae has got a driving mechanism fixed in the cover 1 in a shape close to rectangle equipped with two manipulative holes 3a, 3b, situated in the same lateral wall 2 of the cover 1. The cover 1 is equipped with one open seat 4, in which are placed separated from each other three rotational elements 5a, 5b, 5c of the driving mechanism of various dimensions. Axes 6a, 6b, 6c of rotational elements 5a, 5b, 5c are mounted for an axial movement in the cover 1 perpendicularly to the direction of the displacement of vertebrae against each other, and on the one end of the axis 6*a*, 6*b*, 6*c* of each rotational element 5*a*, 5*b*, 5*c*, situated from the side of manipulative holes 3*a*, 3*b* a gear 12*a*, 12*b*, 12*c* is seated. The central rotational element 5*b* is equipped with anchoring latches 8 in a form of paddles of equal dimensions and shapes, situated on its left side rotational element 5*a* is equipped with anchoring latches 8 in a form of teeth of equal dimensions and shapes, whereas the third rotational element 5*c* is equipped with anchoring latches 8 in a form of spikes of equal dimensions. Anchoring latches 8 on each rotational element 5*a*, 5*b*, 5*c* project over the height of walls 2 of the cover 1 from the side contacting with one of displaced vertebrae and anchor in this vertebra. The driving mechanism has got two connecting elements 7*a*, 7*b*, each having a form of a gear. One connecting element 7*a* is equipped with a plug 13, whereas the second connecting element 7*b* is equipped with a shaped recess 14. Each connecting element 7*a*, 7*b* is situated in the manipulative hole 3*a*, 3*b* of the cover between gears 12*a*, 12*b*, 12*c* seated on selected ends of axis 6*a*, 6*b*, 6*c* of rotational element 5*a*, 5*b*, 5*c* and cooperates with these gears 12*a*, 12*b*, 12*c* and the second connecting element 7*a*, 7*b*. Each connecting element 7*a*, 7*b* cooperates with not visible on the figure separate driving tool. There is a possibility of driving the implant using one of connecting elements 7*a*, 7*b*, depending on the operational field. The blockade of the rotation of the driving element constitutes fixed to the cover 1 latch 9*b* cooperating with one rotational element 5*c*. The lower surface of one of lateral walls 2 of the cover 1 is equipped with anchoring projections 10 in a form of two pairs of spikes, anchoring in the second of displaced vertebrae.

In an embodiment of the invention illustrated on FIG. 24 the intervertebral implant for mutual situating of adjacent vertebrae has got a driving mechanism fixed in the cover 1 in a shape close to the rectangle equipped with two manipulative holes 3*a*, 3*b*, situated in the same lateral wall 2 of the cover 1. The cover 1 is equipped with two open seats 4*a*, 4*b* separated with separating wall 11. In one seat 4*a* are placed separated from each other two rotational elements 5*a*, 5*b* of the driving mechanism with various dimensions. The central rotational element 5*b* is equipped with anchoring latches 8 in a form of paddles of equal dimensions and shapes, and situated on its right side rotational element 5*a* is equipped with anchoring latches 8 in a form of spikes of equal dimensions. Whereas the third rotational element 5*c*, placed in the second seat 4*b*, is formed by seated on a common axis 6*c* three separate parts of equal dimensions, placed in corresponding to them, separated by separating walls 11 sections of the seat 4*b*. Anchoring latches 8 on each separate part of the third rotational element 5*c* have got a form of paddles of equal shapes and dimensions. Anchoring latches 8 on each rotational element 5*a*, 5*b*, 5*c* project over the height of walls 2 of the cover 1 from the side contacting with one of displaced vertebra and anchor in this vertebra. Axes 6*a*, 6*b*, 6*c* of rotational elements 5*a*, 5*b*, 5*c* are mounted for the axial movement in the cover 1 perpendicularly to the direction of displacement of vertebrae according to each other, and on one end of the axis 6*a*, 6*b*, 6*c* of each rotational element 5*a*, 5*b*, 5*c* situated from the side of manipulative holes 3*a*, 3*b*, a gear 12*a*, 12*b*, 12*c* is seated. The driving mechanism has got two connecting elements 7*a*, 7*b*, each having a form of a gear. One connecting element 7*a* is equipped with a plug 13, whereas the second connecting element 7*b* is equipped with a shaped recess 14. Each connecting element 7*a*, 7*b* is situated in the manipulative hole 3*a*, 3*b* of the cover 1 between gears 12*a*, 12*b*, 12*c* seated on selected ends of the axis 6*a*, 6*b*, 6*c* of rotational elements 5*a*, 5*b*, 5*c* and cooperates with these gears 12*a*, 12*b*, 12*c* and the second connecting element 7*a*, 7*b*. Each connecting element 7*a*, 7*b* cooperates with not visible on the figure separate driving tool. There is a possibility of driving the implant using one of connecting elements 7*a*, 7*b*, dependent on the operational field. The blockade of the rotation of the driving element is constituted by fixed to the cover 1 latch 9*b* cooperating with one rotational element 5*a*. The lower surface of one of lateral walls 2 of the cover 1 is equipped with anchoring projections 10 in a form of two pairs of spikes, anchoring in the second of displaced vertebrae.

Illustrated on FIG. 25 intervertebral implant for mutual situating of adjacent vertebrae has got a cover 1 in a shape close to the rectangle, in which is fixed a driving mechanism. In a lateral wall 2 of the cover 1*a* manipulative hole 3 is made. The cover 1 is equipped with one open seat 4. The driving mechanism composes placed in the seat 4 and anchoring in both displaced vertebrae one rotational element 5 with an axis 6 mounted for axial movement in lateral walls 2 of the cover 1 perpendicularly to the direction of the displacement of vertebrae in the relation to each other, cooperating with a connecting element 7. The rotational element 5 is equipped with anchoring latches 8 projecting over the height of lateral walls 2 of the cover 1, which enables anchoring of the rotational element 5 in both displaced vertebrae. Anchoring latches 8 have got a form of paddles of equal shapes and dimensions. The connecting element 7, situated within the diameter of the manipulative hole 3 of the cover 1, cooperates with not visible on the figure separate driving tool. The connecting element 7 composes one shaped end of the axis 6 of the rotational element 5. The implant is equipped with two blockades of the rotation of the driving mechanism. One of the blockades of the rotation of the driving mechanism has got a form of a pin 9*a* situated within the diameter of the manipulative hole 3 of the cover 1 and cooperating with not visible on this figure recess in the axis 6 of the rotational element 5, whereas the second blockade of the rotation composes the latch 9*b* fixed to the cover 1 at the opposite side than the pin 9*a*, cooperating with the rotational element 5.

FIG. 26 shows graphically the displacement of vertebrae V1 and V2 using an intervertebral implant situated between them, having one rotational element 5 fixed in the cover 1. Anchoring latches 8 of the rotational element 5 project over the height of lateral walls 2 of the cover 1 and anchor in both displaced vertebrae V1 and V2. Vertebrae V1 and V2 are displaced in the relation to each other, in the opposite direction, by the movement of anchored in them with anchoring latches 8 rotational element 5. The movement of vertebrae takes place also according to the cover 1, which is connected with none of displaced vertebrae.

On FIG. 27 is graphically illustrated the movement of vertebra V2 in a coronal plane using an intervertebral implant, having fixed in the cover 1 one rotational element 5 and one connecting element 7. Anchoring latches 8 of the rotational element 5 project over the height of lateral walls 2 of the cover 1 and anchor in the vertebra V2 and not visible on the figure second vertebra. The movement of vertebrae takes place also in the relation to the cover 1, which is connected with none of displaced vertebrae.

On FIG. 28 is graphically illustrated the movement of the vertebra V2 in a sagittal plane using an intervertebral implant, having fixed in the cover 1 one rotational element 5 and one connecting element 7. Anchoring latches 8 of the rotational element 5 project over the height of lateral walls 2 of the cover 1 and anchor in the vertebra V2 and not visible on the figure second vertebra. The movement of vertebrae takes place also in the relation to the cover 1, which is connected with none of displaced vertebrae.

FIG. 29 illustrates two blockades of the rotation—one in a form of a latch 9b fixed to the cover 1, cooperating with the rotational element 5 and second in a form of a pin 9a situated within the diameter of the manipulative hole 3 of the cover 1, cooperating with the recess 9c in the axis 6 of the rotational element 5.

In an embodiment illustrated on FIG. 30 the cover in a shape close to the shape of the vertebral body 1 is equipped with two manipulative holes 3 situated symmetrically in lateral walls 2 of the cover 1. Placed in the seat 4 of the cover 1 one rotational element 5 with an axis 6 mounted for the axial movement in lateral walls 2 of the cover 1 perpendicularly to the direction of the displacement of vertebrae in the relation to each other is equipped with anchoring latches 8 projecting over the height of lateral walls 2 of the cover 1 and anchoring in both displaced vertebrae. The rotational element 5 cooperates with two connecting elements 7a, 7b. Each connecting element 7a, 7b is situated within the diameter of one manipulative hole 3 of the cover 1 and cooperates with not visible on the figure separate driving tool. Each connecting element 7a, 7b composes a shaped end of the axis 6 of the rotational element 5, whereas one connecting element 7b has got a form of a shaped element with a hexagonal cross section. Such constructional variant enables driving of the driving element 5 using one of connecting elements 7a, 7b or both simultaneously, depending on the operational field. The implant is equipped with two blockades of the rotation of the driving mechanism. One of blockades of the rotation has got a form of a pin 9a situated within the diameter of the manipulative hole 3 of the cover 1 and cooperating with not visible on this figure recess in the axis 6 of the rotational element 5, whereas the second blockade composes the latch 9b fixed to the cover 1 at the opposite side than the pin 9a, cooperating with the rotational element 5.

In an embodiment of the invention illustrated on FIG. 31 the cover 1 has got a form of a frame of irregular shape provided with one manipulative hole 3. The cover 1 is equipped with two open seats 4a, 4b, in which are placed two rotational elements 5a, 5b of the driving mechanism with various dimensions, separated from each other by a fragment of the cover, provided with anchoring latches 8 projecting over the height of lateral walls 2 of the cover 1 and anchoring in both displaced vertebrae. The axis 6 of each rotational element 5a, 5b is mounted for the axial movement in the cover 1 perpendicularly to the direction of the displacement of vertebrae according to each other. One rotational element 5a cooperates with the connecting element 7 and is equipped with anchoring latches 8 in a form of spikes with equal dimensions. Whereas the second rotational element 5b is equipped with anchoring latches 8 in a form of teeth with a shape close to rectangles of equal dimensions. The connecting element 7 is situated within the diameter of the manipulative hole 3 of the cover 1 and composes a shaped end of the axis 6 of one of rotational elements 5a. The connecting element 7 cooperates with not visible on the figure separate driving tool. The blockade of the rotation of the driving mechanism has got a form of paddles 9d situated on the lateral surface of the rotational element 5a, cooperating with one latch 9b fixed to the lateral wall 2 of the cover 1.

In an embodiment of the invention illustrated on FIG. 32 an intervertebral implant for mutual situating of adjacent vertebrae has got a driving mechanism fixed in the cover 1 with a cross section close to oval, equipped with two manipulative holes 3a, 3b, situated in the same lateral wall 2 of the cover 1. The cover 1 is equipped with two separated from each other with a separating wall 11 open seats 4a, 4b, in which are placed two rotational elements 5a, 5b of a driving mechanism with equal dimensions and shapes, equipped with anchoring latches projecting over the height of lateral walls 2 of the cover 1 and anchoring in both displaced vertebrae. Anchoring latches 8 of each rotational element 5a, 5b have got a form of spikes with equal dimensions and shapes. In each manipulative hole 3a, 3b is situated one connecting element 7a, 7b composing one end of the axis 6 of each rotational element 5a, 5b, with various length. Each connecting element 7a, 7b cooperates with not visible on the figure separate driving tool. Such constructional variant enables driving of rotational elements 5a, 5b using only one of connecting elements 7a, 7b or two simultaneously, dependent on the operational field. The blockade of the rotation of the driving mechanism has got a form of a latch 9b fixed to the lateral wall 2 of the cover 1, cooperating with one rotational element 5a.

In an embodiment of the invention illustrated on FIG. 33 the cover 1 in a shape close to the rectangle is equipped with one manipulative hole 3 and one open seat 4, in which are placed separated from each other two rotational elements 5a, 5b of the driving mechanism. Rotational elements 5a, 5b have got various dimensions and are equipped with anchoring latches 8 projecting over the height of lateral walls 2 of the cover 1, anchoring in both displaced vertebrae. One rotational element 5a is equipped with anchoring latches 8 in a form of paddles of equal dimensions and shapes, whereas the second rotational element 5b is equipped with anchoring latches 8 in a form of spikes of equal dimensions and shapes, situated on a part of the external surface of this rotational element 5b. The axis 6 of the second rotational element 5b composes its separable part, and on its end, situated from the side of the manipulative hole 3, is seated a gear 12 fixed in the cover 1. The driving mechanism has got one connecting element 7 situated in the manipulative hole 3 of the cover 1, having a form of a gear cooperating with the gear 12 seated on selected end of the axis 6 of one rotational element 5b. The connecting element 7 is equipped with a plug 13. The blockade of the rotation of the driving mechanism has got a form of a latch 9b fixed to the lateral wall 2 of the cover 1 cooperating with one rotational element 5a.

In an embodiment of the invention illustrated on FIG. 34 the cover 1 is equipped with one manipulative hole 3 and one open seat 4 divided on three section separated with separating walls 11. Each of two rotational elements 5a, 5b is made of seated on a common axis 6a, 6b three separate parts of equal dimensions, placed in corresponding to them, separated with separating walls 11 sections of the seat 4. Each separate part of each rotational element 5a, 5b is equipped with latches 8 in a form of teeth and spikes of various shapes and dimensions. Anchoring latches 8 project over the height of lateral walls 2 of the cover 1 and anchor in both displaced vertebrae. On one end of the axis 6a, 6b of each rotational element 5a, 5b, situated from the side of the manipulative hole 3, a gear 12, 12b is seated, fixed in the cover 1. The connecting element 7 is situated in the manipulative hole 3 of the cover 1 and cooperates with not visible on the figure separate driving tool. The connecting element 7 has got a form of a gear equipped with a recess 14, cooperating with gears 12a, 12b composing selected ends of the axis 6a, 6b of each rotational element 5a, 5b, seated on its both sides. The blockade of the rotation of the driving mechanism has got a form of one latch 9b fixed to the lateral wall 2 of the cover 1, cooperating with one rotational element 5a.

In an embodiment of the invention illustrated on FIG. 35 each of two rotational elements 5a, 5b is made of seated on a common axis 6a, 6b three separate parts of various dimensions, placed in corresponding to them, separated with separating walls 11 sections of the seat 4, and each separate part of each rotational element 5a, 5b is equipped with anchoring latches 8 in a form of paddles of equal dimensions. Anchoring latches project over the height of lateral walls 2 of the cover 1 and anchor in both displaced vertebrae. On one end of the axis 6a, 6b of each rotational element 5a, 5b, situated from the side of the manipulative hole 3, a gear 12a, 12b is seated, fixed in the cover 1. The connecting element 7 is situated in the manipulative hole 3 of the cover 1 and cooperates with not visible on the figure separate driving tool. The connecting element 7 has got a form of a gear cooperating with gears 12a, 12b composing selected ends of the axis 6a, 6b of each rotational element 5a, 5b, seated on its both sides and is equipped with a plug 13. The blockade of the rotation of the driving mechanism has got a form of one latch 9b fixed to the lateral wall 2 of the cover 1, cooperating with one rotational element 5a.

Illustrated on FIG. 36 rotational element 5 is equipped with anchoring latches 8 in a form of spikes of equal dimensions and shapes. The shaped axis 6 of the rotational element 5 composes its separable part, and the greatest dimension A of the cross section of the axis 6 is bigger than the transverse dimension B of the hole 15 of the rotational element 5.

In an embodiment of the invention illustrated on FIG. 37 the cover 1 is equipped with two manipulating holes 3a, 3b situated in the same lateral wall 2 of the cover 1 and one open seat 4 divided on three sections. In the seat 4 are placed two rotational elements 5a, 5b separated from each other. Each rotational element 5a, 5b is made of seated on a common axis 6a, 6b three separate parts of various dimensions, placed in corresponding to them, separated with separating walls 1 sections of the seat 4. Separate parts of each rotational element 5a, 5b are equipped with anchoring latches 8 of various dimensions and in shapes of the paddles, spikes and teeth. Anchoring latches 8 of rotational elements 5a, 5b project over the height of lateral walls 2 of the cover 1 and anchor in both displaced vertebrae. The implant is equipped with two connecting elements 7a, 7b. Each connecting element 7a, 7b composes one shaped end of the axis 6a, 6b of each rotational element 5a, 5b, situated in one manipulative hole 3a, 3b of the cover 1. The implant is equipped with three blockades of the rotation of the driving mechanism. Each of two blockades of the rotation has got a form of a pin 9a situated within the diameter of selected manipulative hole 3a, 3b of the cover 1, cooperating with not visible on the figure recess in the axis 6a, 6b of selected rotational element 5a, 5b. The third blockade of the rotation has got a form of one latch 9b fixed to the cover 1 and cooperating with one rotational element 5a.

There is a possibility of driving the rotational elements 5a, 5b using one of connecting elements 7a, 7b or two connecting elements 7a, 7b simultaneously, dependent on the operational field.

On FIG. 38-43 are illustrated various embodiments of rotational elements 5 with anchoring latches 8 and various holes 15.

Illustrated on FIG. 38 rotational element 5 is equipped with a shaped hole 15 and anchoring latches 8 in a form of teeth and spikes of equal dimensions.

Illustrated on FIG. 39 rotational element 5 is equipped with a shaped hole 15 and anchoring latches 8 in a form of teeth and paddles of various dimensions and shapes.

Illustrated on FIG. 40 rotational element 5 is equipped with a shaped hole 15 and anchoring latches 8 in a form of latches of equal shapes and dimensions. The lateral surface of the rotational element 5 is equipped with teeth 9e, composing the element of the blockade of the rotation of the driving mechanism.

Illustrated on FIG. 41 rotational element 5 is equipped with a circular hole 15 and anchoring latches 8 in a form of spikes of equal dimensions, made on a part of the surface of the rotational element 5.

Illustrated on FIG. 42 rotational element 5 is equipped with a circular hole 15 and anchoring latches 8 in a form of paddles of various dimensions. The lateral surface of the rotational element 5 is provided with paddles 9d, composing the element of the blockade of the rotation of the driving mechanism.

Illustrated on FIG. 43 rotational element has got a conical shape and is equipped with a shaped hole 15 and anchoring latches 8 in a form of teeth of equal shapes and various dimensions.

Illustrated on FIG. 44 rotational element 5 is equipped with anchoring latches 8 in a form of paddles of equal shapes and dimensions. The axis 6 of the rotational element 5 has got a circular cross section and composes its inseparable part.

Illustrated on FIG. 45 rotational element 5 is equipped with anchoring latches 8 in a form of teeth of equal shapes and dimensions. The shaped axis 6 is fixed separable in the rotational element 5. In the axis 6 of the rotational element 5 a recess 9c is made.

In an embodiment of the invention illustrated on FIG. 46 the cover 1 has got a form of a frame of irregular shape, provided with two manipulative holes 3a, 3b situated in the same lateral wall 2 of the cover 1. The cover 1 is equipped with two open seats 4a, 4b, in which are placed separated from each other with a fragment of the cover 1 two rotational elements 5a, 5b of the driving mechanism of various dimensions, cooperating with two connecting elements 7a, 7b. Each rotational element 5a, 5b cooperates with one connecting element 7a, 7b. One rotational element 5a is equipped with anchoring latches 8 in a form of spikes of various dimensions, whereas the second rotational element 5b has got a form close to the cone narrowing towards the connecting element 7b and is equipped with anchoring latches 8 in a form of teeth in a shape close to rectangles of various dimensions. Anchoring latches on each rotational element 5a, 5b project over the height of lateral walls 2 of the cover 1 and anchor in both displaced vertebrae. Each connecting element 7a, 7b is situated within the diameter of the manipulative hole 3a, 3b of the cover 1 and cooperates with not visible on the figure separate driving tool. Each connecting element 7a, 7b composes one shaped end of the axis 6a, 6b of each rotational element 5a, 5b. There is a possibility of driving the implant using one of connecting elements 7a, 7b, depending on the operational field. The blockade of the rotation has got a form of holes 9f made on the lateral surface of one rotational element 5a, cooperating with the latch 9b. The latch 9b is fixed to the lateral wall 2 of the cover 1 and cooperates with the rotational element 5a equipped with anchoring latches 8 in a form of teeth in a shape of cones.

In an embodiment of the invention illustrated on FIG. 47 the intervertebral implant for mutual situating adjacent vertebrae has got a driving mechanism fixed in the cover 1 in a shape close to the rectangle, provided with two manipulative holes 3a, 3b, situated in the same lateral wall 2 of the cover 1. The cover 1 is equipped with one open seat 4, in which are placed separated from each other three rotational elements 5a, 5b, 5c of the driving mechanism of various dimensions. Axes 6a, 6b and 6c of rotational elements 5a, 5b, 5c are mounted for an axial movement in the cover 1 perpendicularly to the direction of displacement of vertebrae in the relation to each other, and on one end of the axis 6a, 6b, 6c of each rotational element 5a, 5b, 5c, situated from the side of manipulative holes 3a, 3b, is seated a gear 12a, 12b, 12c.

Central rotational element 5b is equipped with anchoring latches 8 in a form of paddles of equal dimensions and shapes, located on its left side rotational element 5a is equipped with anchoring latches 8 in a form of teeth of equal dimensions and shapes, whereas the third rotational element 5c is equipped with anchoring latches 8 in a form of spikes of equal dimensions. Anchoring latches 8 on each rotational element 5a, 5b, 5c project over the height of lateral walls 2 of the cover 1 and anchor in both displaced vertebrae. The driving mechanism has got two connecting elements 7a, 7b, each having a form of a gear. One connecting element 7a is equipped with a plug 13, whereas the second connecting element 7b is equipped with a shaped recess 14. Each connecting element 7a, 7b is situated in the manipulative hole 3a, 3b of the cover 1 between gears 12a, 12b, 12c seated on selected ends of axes 6a, 6b, 6c of rotational element 5a, 5b, 5c and cooperates with these gears 12a, 12b, 12c and the second connecting element 7a, 7b. Each connecting element 7a, 7b cooperates with not visible on the figure separate driving element. There is a possibility of driving the implant using one of connecting elements 7a, 7b, dependent on operational field. The blockade of the rotation of the driving mechanism composes fixed to the cover latch 9b cooperating with one rotational element 5c.

In an embodiment of the invention illustrated on FIG. 48 the intervertebral implant for mutual situating of adjacent vertebrae has got a driving mechanism fixed in the cover 1 in a shape close to the rectangle provided with two manipulative holes 3a, 3b, situated in the same lateral wall 2 of the cover 1. The cover 1 is equipped with two open seats 4a, 4b separated with separating wall 11. In one seat 4a are placed separated from each other two rotational elements 5a, 5b of the driving mechanism of various dimensions. The central rotational element 5b is equipped with anchoring latches of equal dimensions and shapes, and located on its right side rotational element 5a is equipped with anchoring latches 8 in a form of spikes of equal dimensions. Whereas the third rotational element 5c, placed in the second seat 4b, is made of seated on a common axis 6c three separate parts of equal dimensions, placed in corresponding to them, separated with separating walls 11 sections of the seat 4b. Anchoring latches 8 on each separate part of the third rotational element 5c have got a form of paddles of equal dimensions and shapes. Anchoring latches 8 on each rotational element 5a, 5b, 5c project over the height of lateral walls 2 of the cover 1 and anchor in both displaced vertebrae. Axes 6a, 6b, 6c of rotational elements 5a, 5b, 5c are mounted for an axial movement in the cover 1 perpendicularly to the direction of displacement of vertebrae in the relation to each other, and on one end of the axis 6a, 6b, 6c of each rotational element 5a, 5b, 5c, situated from the side of manipulative holes 3a, 3b, a gear 12a, 12b, 12c is seated. The driving mechanism has got two connecting elements 7a, 7b, each having a form of a gear. One connecting element 7a is equipped with a plug 12, whereas the second connecting element 7b is equipped with a shaped recess 14. Each connecting element 7a, 7b is situated in the manipulative hole 3a, 3b of the cover 1 between gears 12a, 12b, 12c seated on selected ends of axes 6a, 6b, 6c of rotational elements 5a, 5b, 5c and cooperates with these gears 12a, 12b, 12c and the second connecting element 7a, 7b. Each connecting element 7a, 7b cooperates with not visible on the figure separate driving tool. There is a possibility of driving the implant using one of connecting elements 7a, 7b, dependent on the operational field. The blockade of the rotation of the driving mechanism composes fixed to the cover 1 latch 9b cooperating with one rotational element 5a.

The invention may, in particular, be realized according to the following clauses:

1. Intervertebral implant for mutual situating of adjacent vertebrae containing a driving mechanism fixed in a cover provided with at least one manipulative hole, where the cover (1) is provided with at least one open seat (4) and the driving mechanism comprises located in the seat (4) and anchoring in one of displaced vertebrae at least one rotational element (5) with an axis (6) mounted for an axial movement in lateral cover's (1) walls (2) in a perpendicular manner to the direction of mutual displacement of vertebrae, equipped with anchoring latches (8) projecting over the height of the cover's (1) wall (2), cooperating with at least one connecting element (7) situated within the diameter of the selected manipulative hole (3) of the cover (1), whereby the cover (1) is equipped with at least one anchoring projection (10) anchoring in the second displaced vertebra, and the implant is provided with at least one blockade of the rotation of the driving mechanism.
2. Intervertebral implant according to clause 1 is characterized in that rotational elements (5a, 5b, 5c) are separated from each other.
3. Intervertebral implant according to clause 1 or 2 is characterized in that rotational elements (5a, 5b, 5c) of the driving mechanism have various dimensions.
4. Intervertebral implant according to clauses 1-3 is characterized in that anchoring latches (8) situated in the rotational element (5) have various dimensions.
5. Intervertebral implant according to clauses 1-4 is characterized in that anchoring latches (8) situated on the rotational element (5) have various shapes.
6. Intervertebral implant according to clauses 1-3 is characterized in that the rotational element (5) is formed of seated on a common axis (6) separate parts situated in corresponding to them, separated with at least one separating wall (11), sections of the seat (4).
7. Intervertebral implant according to clause 6 is characterized in that separate parts of the rotational element (5) have various dimensions.
8. Intervertebral implant according to clause 6 or 7 is characterized in that anchoring latches (8) situated on a separate part of the anchoring element (5) have various dimensions.
9. Intervertebral implant according to clauses 6-8 is characterized in that anchoring latches (8) situated on a separate part of the rotational element (5) have various shapes.
10. Intervertebral implant according to clauses 1-9 is characterized in that the axis (6) of the rotational element (5) has got a circular cross-section.
11. Intervertebral implant according to clauses 1-9 is characterized in that the axis (6) of the rotational element (5) has got a shaped cross-section.
12. Intervertebral implant according to clause 11 is characterized in that the axis (6) of the rotational element (5) constitutes its separable part.
13. Intervertebral implant according to clause 12 is characterized in that the greatest dimension A of the cross-section of the axis (6) is greater than the transverse dimension B of the hole (15) of the rotational element (5).
14. Intervertebral implant according clause 10-13 is characterized in that at least one end of the axis (6) of at least one rotational element (5) has got a form of a shaped element.
15. Intervertebral implant according to clauses 1-15 is characterized in that on at least one end of the axis (6) of at least one rotational element (5) at least one gear (12) is seated.
16. Intervertebral implant according to clauses 1-15 is characterized in that connecting element (7) cooperates with a separate driving tool.

17. Intervertebral implant according to clause 15 or 16 is characterized in that the connecting element (7) has got the form of a gear cooperating with the gear (12) seated on the selected end of the axis (6) of at least one rotational element (5).

18. Intervertebral implant according to clause 16 or 17 is characterized in that connecting element (7) constitutes at least one end of the axis (6) of at least one rotational element (5).

19. Intervertebral implant according to clauses 16-18 is characterized in that connecting element (7) is equipped with the plug (13).

20. Intervertebral implant according to clauses 1-19 is characterized in that anchoring projections (10) have various dimensions.

21. Intervertebral implant according to clauses 1-19 is characterized in that anchoring projections (10) have various shapes.

22. Intervertebral implant according to clauses 1-21 is characterized in that the blockade of the rotation has got a form of a pin (9a) situated inside the diameter of the cover's (1) manipulative hole (3) and cooperating with the recess (9c) in the axis (6) of the rotational element (5).

23. Intervertebral implant according to clauses 1-21 is characterized in that the blockade of the rotation of the driving mechanism has got a form of at least one latch (9b) fixed to the cover (1) and cooperating with at least one rotational element (5).

24. Intervertebral implant according to clause 23 is characterized in that the blockade of the rotation has got a form of paddles (9d) situated on a lateral surface of the rotational element (5) cooperating with at least one latch (9b).

25. Intervertebral implant according to clause 23 is characterized in that the blockade of the rotation has got a form of teeth (9e) situated on a lateral surface of the rotational element (5) cooperating with at least one latch (9b).

26. Intervertebral implant according to clause 23 is characterized in that the blockade of the rotation has got a form of holes (9f) performed on a lateral surface of the rotational element (5) cooperating with at least one latch (9b).

27. Intervertebral implant for mutual situating of adjacent vertebrae containing a driving mechanism fixed in a cover provided with at least one manipulative hole, where the cover (1) is provided with at least one open seat (4) and the driving mechanism comprises located in the seat (4) and anchoring in both displaced vertebrae at least one rotational element (5) with an axis (6) mounted for an axial movement in lateral cover's (1) walls (2) in a perpendicular manner to the direction of mutual displacement of vertebrae, equipped with anchoring latches (8) projecting over the height of the cover's (1) lateral walls (2), cooperating with at least one connecting element (7) situated inside the diameter of the selected manipulative hole (3) of the cover (1), whereby the implant is provided with at least one blockade of the rotation of the driving mechanism.

28. Intervertebral implant according to clause 27 is characterized in that rotational elements (5a, 5b, 5c) are separated from each other.

29. Intervertebral implant according to clause 27 or 28 is characterized in that rotational elements (5a, 5b, 5c) of the driving mechanism have various dimensions.

30. Intervertebral implant according to clauses 27-29 is characterized in that anchoring latches (8) situated on the rotational element (5) have various dimensions.

31. Intervertebral implant according to clauses 27-30 is characterized in that anchoring latches (8) situated on the rotational element (5) have various shapes.

32. Intervertebral implant according to clauses 27-29 is characterized in that the rotational element (5) is formed on seated on a common axis (6) separate parts located in corresponding to them separate parts separated with at least one separating wall (11), sections of the seat (4).

33. Intervertebral implant according to clause 32 is characterized in that the separate parts of the rotational element (5) have various dimensions.

34. Intervertebral implant according to clause 32 or 33 is characterized in that anchoring latches (8) situated on the separate part of the rotational element (5) have various dimensions.

35. Intervertebral implant according to clauses 32-34 is characterized in that anchoring latches (8) situated on the separate part of the rotational element (5) have various shapes.

36. Intervertebral implant according to clauses 27-35 is characterized in that the axis (6) of the rotational element (5) have a circular cross-section.

37. Intervertebral implant according to clauses 27-35 is characterized in that the axis (6) of the rotational element (5) have a shaped cross-section.

38. Intervertebral implant according to clause 37 is characterized in that the axis (6) of the rotational element (5) constitutes its separable part.

39. Intervertebral implant according to clause 38 is characterized in that the greatest dimension A of the cross-section of the axis (6) is greater than the transverse dimension B of the hole (15) of the rotational element (5).

40. Intervertebral implant according clauses 36-39 is characterized in that at least one end of the axis (6) of at least one rotational element (5) has got a form of a shaped element.

41. Intervertebral implant according to clauses 36-40 is characterized in that on at least one end of the axis (6) of at least one rotational element (5) at least one gear (12) is seated.

42. Intervertebral implant according to clauses 27-41 is characterized in that the connecting element (7) cooperates with a separate driving tool.

43. Intervertebral implant according to clause 41 or 42 is characterized in that the connecting element (7) has got the form of a gear cooperating with the gear (12) seated on the selected end of the axis (6) of at least one rotational element (5).

44. Intervertebral implant according to clause 42 or 43 is characterized in that the connecting element (7) constitutes at least one end of the axis (6) of at least one rotational element (5).

45. Intervertebral implant according to clauses 42-44 is characterized in that the connecting element (7) is equipped with the plug (13).

46. Intervertebral implant according to clauses 27-45 is characterized in that the blockade of the rotation has got a form of a pin (9a) situated inside the diameter of the cover's (1) manipulative hole (3) and cooperating with the recess (9c) in the axis (6) of the rotational element (5).

47. Intervertebral implant according to clauses 27-45 is characterized in that the blockade of the rotation of the driving mechanism has got a form of at least one latch (9b) fixed to the cover (1) and cooperating with at least one rotational element (5).

48. Intervertebral implant according to clause 47 is characterized in that the blockade of the rotation has got a form of paddles (9d) situated on a lateral surface of the rotational element (5) cooperating with at least one latch (9b).

49. Intervertebral implant according to clause 47 is characterized in that the blockade of the rotation has got a form of teeth (9e) situated on a lateral surface of the rotational element (5) cooperating with at least one latch (9b).

50. Intervertebral implant according to clause 47 is characterized in that the blockade of the rotation has got a form of holes (9f) performed on a lateral surface of the rotational element (5) cooperating with at least one latch (9b).

The invention claimed is:
1. Intervertebral implant for mutual situating of adjacent vertebrae, said intervertebral implant comprising:
   a cover;
   a driving mechanism fixed in the cover,
   said cover being provided with a cover wall that presents a manipulative hole,
   said cover being further provided with an open seat,
   said driving mechanism including a rotational element with an axis, said rotational element being located in the seat and continuously rotatable about the axis,
   said rotational element being equipped with anchoring latches or groups of anchoring latches that project in an engagement direction over a height of the cover wall to provide exposed latches that engage at least one of the vertebrae, where the anchoring latches or the groups of anchoring latches extend parallel to the axis of the rotational element,
   said rotational element cooperating with a connecting element situated within the manipulative hole of the cover wall; and
   a blockade simultaneously permitting continuous rotation of the driving mechanism in a first direction and operable to selectively bock rotation thereof in a second direction,
   said exposed latches moving along a common direction relative to the cover when the rotational element is continuously rotated so that the implant moves the vertebrae horizontally relative to each other.
2. The intervertebral implant as claimed in claim 1,
   said cover being equipped with at least one anchoring projection projecting over the cover wall in a direction opposite to the engagement direction in which the anchoring latches or groups of anchoring latches of the rotational element project over the cover wall, with the exposed latches operable to engage one of the vertebrae and the at least one anchoring projection operable to engage the other one of the vertebrae.
3. The intervertebral implant as claimed in claim 1,
   said anchoring latches or groups of anchoring latches of the rotational element projecting over the cover wall in two directions opposite to each other.
4. The intervertebral implant as claimed in claim 1,
   said driving mechanism including a plurality of rotational elements that include the first-mentioned rotational element, with the plurality of rotational elements being separated from each other.
5. The intervertebral implant as claimed in claim 1,
   said driving mechanism comprising a plurality of rotational elements including the first-mentioned rotational element, with the plurality of rotational elements having various dimensions.
6. The intervertebral implant as claimed in claim 1,
   said anchoring latches situated in the rotational element having various dimensions.
7. The intervertebral implant as claimed in claim 1,
   said anchoring latches situated on the rotational element having various shapes.
8. The intervertebral implant as claimed in claim 1,
   said rotational element being formed of separate parts seated on a common axis and separated by at least one separating wall.
9. The intervertebral implant as claimed in claim 8,
   said separate parts of the rotational element having various dimensions.
10. The intervertebral implant as claimed in claim 8,
   said anchoring latches situated on one of the separate parts of the rotational element having various dimensions.
11. The intervertebral implant as claimed in claim 8,
   said anchoring latches situated on one of the separate parts of the rotational element having various shapes.
12. The intervertebral implant as claimed in claim 1,
   said axis of the rotational element presenting a circular cross-section.
13. The intervertebral implant as claimed in claim 1,
   said axis of the rotational element presenting a shaped cross-section.
14. The intervertebral implant as claimed in claim 13,
   said axis of the rotational element constitutes a separable part.
15. The intervertebral implant as claimed in claim 14,
   said shaped cross-section of the axis defining a greatest dimension and said rotational element presenting a hole that defines a transverse dimension, with the greatest dimension of the axis being greater than the transverse dimension of the hole of the rotational element.
16. The intervertebral implant as claimed in claim 1,
   at least one end of said axis of the rotational element having a form of a shaped element.
17. The intervertebral implant as claimed in claim 1; and
   at least one gear being seated on at least one end of the axis of the rotational element.
18. The intervertebral implant as claimed in claim 17,
   said connecting element configured to cooperate with a separate driving tool.
19. The intervertebral implant as claimed in claim 17,
   said connecting element having the form of a gear that cooperates with the at least one gear seated on the at least one end of the axis of the rotational element.
20. The intervertebral implant as claimed in claim 19,
   said connecting element defining at least one end of the axis of the rotational element.
21. The intervertebral implant as claimed in claim 20,
   said connecting element including a plug.
22. The intervertebral implant as claimed in claim 1,
   said cover including anchoring projections that present various dimensions.
23. The intervertebral implant as claimed in claim 1,
   said cover including anchoring projections that present various shapes.
24. The intervertebral implant as claimed in claim 1,
   said blockade having a form of a pin situated inside the manipulative hole,
   said axis of the rotational element presenting a recess, with the pin cooperating with the recess in the axis of the rotational element.
25. The intervertebral implant as claimed in claim 1,
   said blockade having a form of at least one latch fixed to the cover and cooperating with the rotational element.
26. The intervertebral implant as claimed in claim 25,
   said blockade having a form of paddles situated on a lateral surface of the rotational element, with the paddles cooperating with the at least one latch.
27. The intervertebral implant as claimed in claim 25,
   said blockade having a form of teeth situated on a lateral surface of the rotational element, with the teeth cooperating with the at least one latch.

28. The intervertebral implant as claimed in claim 25, said blockade having a form of holes defined on a lateral surface of the rotational element, with the holes cooperating with the at least one latch.

* * * * *